United States Patent
Ito et al.

(10) Patent No.: US 12,102,306 B2
(45) Date of Patent: Oct. 1, 2024

(54) ABLATION-TREATMENT-TOOL CONTROL DEVICE, ABLATION SYSTEM, AND ILEAL-MUCOSA ABLATION TREATMENT METHOD

(71) Applicant: OLYMPUS CORPORATION, Tokyo (JP)

(72) Inventors: Ryosuke Ito, Tokyo (JP); Yohei Tanikawa, Tokyo (JP); Asuka Nakamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1016 days.

(21) Appl. No.: 17/076,003

(22) Filed: Oct. 21, 2020

(65) Prior Publication Data

US 2021/0045727 A1 Feb. 18, 2021

Related U.S. Application Data

(63) Continuation of application No. PCT/JP2018/018111, filed on May 10, 2018.

(51) Int. Cl.
*A61B 18/12* (2006.01)
*A61B 17/00* (2006.01)
(Continued)

(52) U.S. Cl.
CPC ............. *A61B 17/00234* (2013.01); *A61B 17/320068* (2013.01); *A61B 18/08* (2013.01);
(Continued)

(58) Field of Classification Search
CPC .... A61B 17/00234; A61B 2017/00017; A61B 2017/00115; A61B 2017/00818;
(Continued)

(56) References Cited

U.S. PATENT DOCUMENTS

| 8,641,711 B2 | 2/2014 | Kelly et al. |
| 9,393,068 B1 | 7/2016 | Leo et al. |

(Continued)

FOREIGN PATENT DOCUMENTS

| AU | 200238241 A1 | 7/2003 |
| WO | 2015/038973 A1 | 3/2015 |

OTHER PUBLICATIONS

International Search Report dated Jul. 17, 2018 issued in PCT/JP2018/018111 (with partial machine translation).

*Primary Examiner* — Thomas A Giuliani
(74) *Attorney, Agent, or Firm* — Scully, Scott, Murphy & Presser, P.C.

(57) ABSTRACT

A control device for an ablation treatment tool includes: a target-value storage unit that stores a target value for the total treatment area; an energy-source output unit that outputs, to the ablation treatment tool, an energy source for performing ablation treatment; an area calculation unit that calculates the total treatment area of the ileal mucosa on which the ablation treatment has been performed; and a control unit that controls termination of the ablation treatment performed by the ablation treatment tool. The control unit notifies an operator of the termination of the ablation treatment or stops the output of the energy source from the energy-source output unit when the calculated total treatment area of the ileal mucosa becomes equal to or greater than the target value.

10 Claims, 17 Drawing Sheets

(51) Int. Cl.
  *A61B 17/32* (2006.01)
  *A61B 18/08* (2006.01)
  *A61B 18/14* (2006.01)
  *A61B 18/20* (2006.01)
  *A61B 18/00* (2006.01)

(52) U.S. Cl.
  CPC .............. *A61B 18/14* (2013.01); *A61B 18/20* (2013.01); *A61B 2017/00017* (2013.01); *A61B 2017/00115* (2013.01); *A61B 2017/00818* (2013.01); *A61B 2017/320069* (2017.08); *A61B 2018/0022* (2013.01); *A61B 2018/00494* (2013.01); *A61B 2018/00577* (2013.01)

(58) Field of Classification Search
  CPC ........ A61B 2017/320069; A61B 18/08; A61B 18/14; A61B 18/20; A61B 18/042; A61B 18/1492; A61B 18/082; A61B 18/1206; A61B 18/1402; A61B 2018/00988; A61B 2018/00702; A61B 2018/00898; A61B 2018/00666; A61B 2018/00684; A61B 2018/00494; A61B 2018/00577; A61B 2018/00642; A61B 2018/00678; A61B 2018/00672; A61B 2018/00708; A61B 2018/00982; A61B 2018/00636
  USPC ........ 606/29, 34, 38, 41, 42, 46; 607/98, 99, 607/101, 113, 115, 116
  See application file for complete search history.

(56) References Cited

U.S. PATENT DOCUMENTS

| | | |
|---|---|---|
| 9,993,281 B2 | 6/2018 | Kelly et al. |
| 2003/0153905 A1 | 8/2003 | Edwards et al. |
| 2008/0275445 A1 | 11/2008 | Kelly et al. |
| 2010/0274239 A1* | 10/2010 | Paul .................. A61B 18/1233 606/42 |
| 2013/0345670 A1 | 12/2013 | Rajagopalan et al. |
| 2014/0088581 A1 | 3/2014 | Kelly et al. |
| 2016/0354144 A1 | 12/2016 | Caplan et al. |
| 2017/0007323 A1 | 1/2017 | Leo et al. |
| 2017/0049523 A1* | 2/2017 | Yoshii ................ A61B 1/00137 |
| 2017/0095136 A1* | 4/2017 | Minamizato ......... A61B 1/0005 |
| 2019/0110835 A1 | 4/2019 | Leo et al. |

* cited by examiner

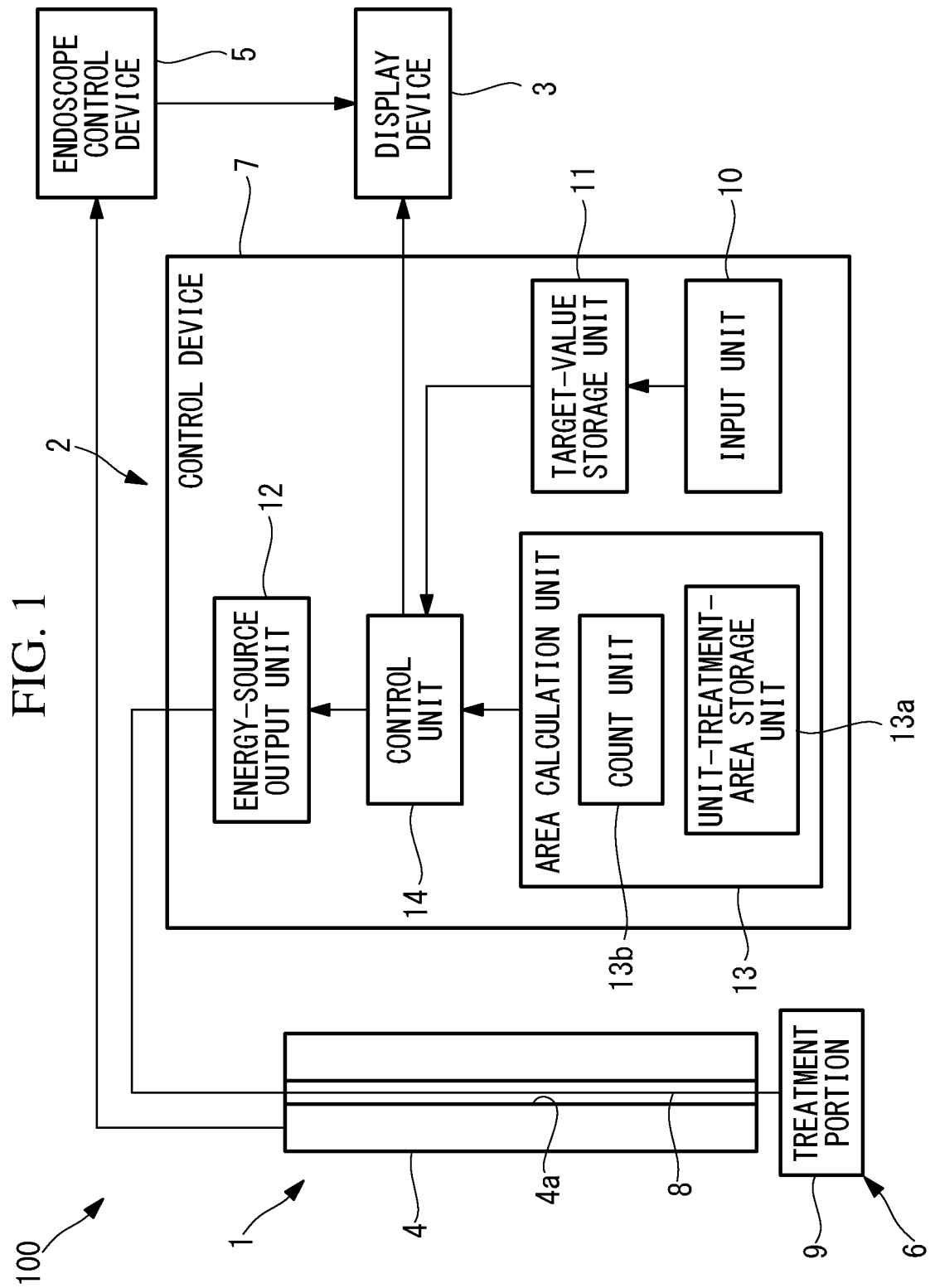

ABLATION-TREATMENT-TOOL CONTROL DEVICE, ABLATION SYSTEM, AND ILEAL-MUCOSA ABLATION TREATMENT METHOD

CROSS-REFERENCE TO RELATED APPLICATIONS

This is a continuation of International Application PCT/JP2018/018111, with an international filing date of May 10, 2018, which is hereby incorporated by reference herein in its entirety.

TECHNICAL FIELD

The present invention relates to an ablation-treatment-tool control device, an ablation system, and an ileal-mucosa ablation treatment method.

BACKGROUND ART

In the related art, there is a known method for performing ablation treatment on the mucous membrane of the duodenum or the jejunum, as a treatment method for obesity and type 2 diabetes (for example, see PTL 1 and PTL 2). Through the ablation treatment of the mucous membrane of the duodenum or the jejunum, absorption of nutrients and lipids is inhibited, thereby making it possible to improve obesity and type 2 diabetes.

CITATION LIST

Patent Literature

{PTL 1} Publication of U.S. Patent Application No. 2013/345670
{PTL 2} U.S. Pat. No. 8,641,711

SUMMARY OF INVENTION

In order to achieve the above-described object, the present invention provides the following solutions.

According to a first aspect, the present invention provides an ablation-treatment-tool control device that controls an ablation treatment tool that performs ablation treatment on ileal mucosa, which covers an inner surface of the ileum, the control device including: a target-value storage unit that stores a target value for the total treatment area of the ileal mucosa, the target value being set on the basis of at least one of the characteristics and the conditions of a patient; an energy-source output unit that outputs, to the ablation treatment tool, an energy source for performing the ablation treatment; an area calculation unit that calculates the total treatment area, which is the total of the areas of treatment regions of the ileal mucosa on which the ablation treatment has been performed by the ablation treatment tool; and a control unit that controls termination of the ablation treatment of the ileal mucosa performed by the ablation treatment tool, wherein the control unit notifies an operator of the termination of the ablation treatment or stops the output of the energy source from the energy-source output unit when the calculated total treatment area of the ileal mucosa becomes equal to or greater than the target value.

According to a second aspect, the present invention provides an ablation-treatment-tool control device that controls an ablation treatment tool that performs ablation treatment on ileal mucosa, which covers an inner surface of the ileum, the control device including: a target-value storage unit that stores a target value for the total treatment area of the ileal mucosa, the target value being set on the basis of at least one of the characteristics and the conditions of a patient; an energy-source output unit that outputs, to the ablation treatment tool, an energy source for performing the ablation treatment; an area calculation unit that calculates the total treatment area, which is the total of the areas of treatment regions of the ileal mucosa on which the ablation treatment has been performed by the ablation treatment tool; and a control unit that controls termination of the ablation treatment of the ileal mucosa performed by the ablation treatment tool, wherein the control unit notifies an operator of the termination of the ablation treatment or stops the output of the energy source from the energy-source output unit when an area that is obtained by subtracting the target value from the sum of the calculated total treatment area of the ileal mucosa and the area of the next single treatment region becomes equal to or greater than an area equal to a predetermined ratio of the area of the next single treatment region.

According to a third aspect, the present invention provides an ablation system including: an ablation treatment tool; and one of the above-described control devices, which control the ablation treatment tool.

According to a fourth aspect, the present invention provides an ileal-mucosa ablation treatment method that is an ablation treatment method for ileal mucosa, which covers an inner surface of the ileum, the method including: a step of setting a target value for the total treatment area of the ileal mucosa, the target value being set on the basis of at least one of the characteristics and the conditions of a patient; a step of repeatedly performing ablation treatment on the ileal mucosa while changing a treatment region; a step of calculating the total treatment area, which is the total of the areas of treatment regions of the ileal mucosa on which the ablation treatment has been performed; and a step of terminating the ablation treatment when the calculated total treatment area of the ileal mucosa becomes equal to or greater than the target value.

According to a fifth aspect, the present invention provides an ileal-mucosa ablation treatment method that is an ablation treatment method for ileal mucosa, which covers an inner surface of the ileum, the method including: a step of setting a target value for the total treatment area of the ileal mucosa, the target value being set on the basis of at least one of the characteristics and the conditions of a patient; a step of repeatedly performing ablation treatment on the ileal mucosa while changing a treatment region; a step of calculating the total treatment area, which is the total of the areas of treatment regions of the ileal mucosa on which the ablation treatment has been performed; and a step of terminating the ablation treatment when an area that is obtained by subtracting the target value from the sum of the calculated total treatment area of the ileal mucosa and the area of the next single treatment region becomes equal to or greater than an area equal to a predetermined ratio of the area of the next single treatment region.

BRIEF DESCRIPTION OF DRAWINGS

FIG. 1 is a diagram showing the overall configuration of an ablation system according to a first embodiment of the present invention.

DESCRIPTION OF EMBODIMENTS

First Embodiment

Figure 2A:
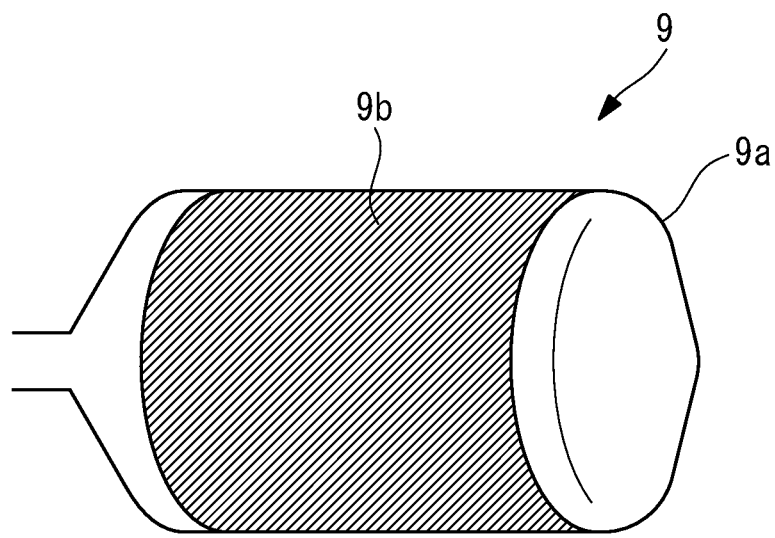
FIG. 2A is a view showing an example configuration of a treatment portion of an ablation treatment tool shown in FIG. 1.

An ablation system 100 and an ablation treatment method according to a first embodiment of the present invention will be described below with reference to the drawings.

The ablation system 100 and the ablation treatment method of this embodiment are applied to a treatment for patients suffering from metabolic diseases (metabolic syndrome), such as diabetes. The small intestine includes the jejunum, which is connected to the duodenum, and the ileum, which is connected to the large intestine. The end section of the ileum has a function of absorbing bile acids. Bile acids are components of bile and function to control the glucose metabolism. Through ablation treatment of the ileal mucosa that covers the inner surface of the ileum, the bile-acid absorption function of the ileum is adjusted, thereby making it possible to improve metabolic diseases.

As shown in FIG. 1, the ablation system 100 includes an endoscope device 1, an ablation-treatment device 2, and a display device 3.

The endoscope device 1 includes a flexible endoscope 4 used for the digestive tract and an endoscope control device 5 that controls the endoscope 4. The endoscope 4 has a treatment-tool channel 4a that penetrates therethrough in the longitudinal direction and through which an ablation treatment tool 6 is inserted.

The ablation-treatment device 2 includes the ablation treatment tool 6 and a control device 7 that controls the ablation treatment tool 6.

The ablation treatment tool 6 includes a long flexible insertion portion 8 that can be inserted through the treatment-tool channel 4a and a treatment portion 9 that is provided at a distal end of the insertion portion 8.

The treatment portion 9 is a portion used to perform ablation treatment on the ileal mucosa. The "ablation treatment" is treatment for degenerating epithelial cells present in the ileal mucosa or for removing the epithelial cells from the ileal mucosa. The "degeneration" means a sufficient change in cell quality to impair the natural bile-acid absorption function of the epithelial cells.

Figure 3A:
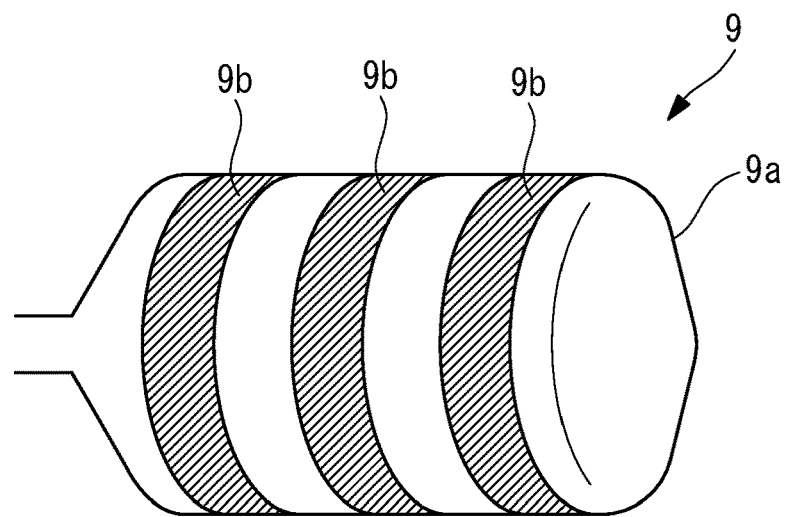
FIG. 3A is a view showing another example configuration of the treatment portion shown in FIG. 1.

As shown in FIGS. 2A and 3A, the treatment portion 9 includes a balloon 9a and at least one ablation part 9b that is provided on an outer circumferential surface of the balloon 9a. A channel (not shown) that communicates with the inside of the balloon 9a is provided in the insertion portion 8. The balloon 9a expands in radial directions perpendicular to the longitudinal axis of the insertion portion 8 when a fluid is supplied thereto via the channel, and contracts in the radial directions when the fluid is discharged therefrom via the channel. In an expanded state, the balloon 9a has an outer diameter equal to or greater than an inner diameter of the ileum. Therefore, in the ileum, the entire outer circumferential surface of the expanded balloon 9a is brought into contact with the ileal mucosa.

The ablation part 9b is provided along the outer surface of the balloon 9a over the entire circumferential direction of the balloon 9a. The ablation part 9b releases energy when an energy source is supplied thereto from an energy-source output unit 12 of the control device 7. The energy is, for example, high-frequency current, radio-frequency current, argon plasma, laser light, ultrasound, or heat. The specific configuration of the ablation part 9b is designed in accordance with the type of the energy. The ablation part 9b is, for example, a discharge electrode, an emission window through which light is emitted, an ultrasonic transducer, or a heating electrode. When the energy is heat, the entire balloon 9a may be configured to function as the ablation part 9b and to be heated.

The energy released from the ablation part 9b is supplied to a region of the ileal mucosa that is in contact with the outer surface of the ablation part 9b, thus making the region of the ileal mucosa generate heat and degenerating the epithelial cells in the region of the ileal mucosa with the heat. Accordingly, ablation treatment is performed on the contact region of the ileal mucosa with the ablation part 9b. The total area of the outer surface of the ablation part 9b is a unit treatment area, that is, the treatment area per single ablation treatment.

Figure 2B:
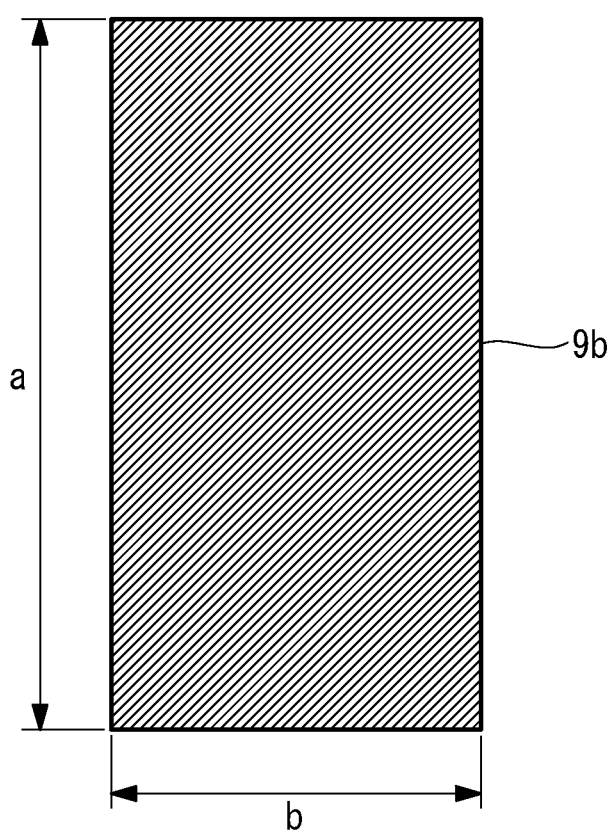
FIG. 2B is a view of an ablation part of the treatment portion shown in FIG. 2A, showing the ablation part developed onto a plane.
Figure 3B:
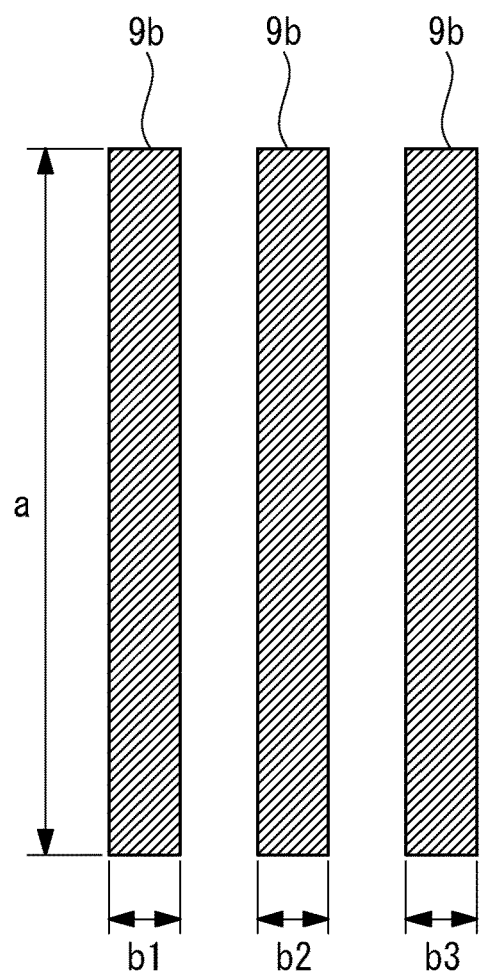
FIG. 3B is a view of ablation parts of the treatment portion shown in FIG. 3A, showing the ablation parts developed onto a plane.

The treatment portion 9 may be provided with a single ablation part 9b, as shown in FIG. 2A, or may be provided with a plurality of ablation parts 9b that are arranged at intervals in the direction along the longitudinal axis of the insertion portion 8, as shown in FIG. 3A. The unit treatment area of the treatment portion 9 shown in FIG. 2A is obtained by a×b, as shown in FIG. 2B. The unit treatment area of the treatment portion 9 shown in FIG. 3A is obtained by a×(b1+b2+b3), as shown in FIG. 3B. In the case of the treatment portion 9 shown in FIG. 3A, because regions of the ileal mucosa that are located between the ablation parts 9b are maintained normal, it is possible to obtain an advantageous effect in that curing is fast, compared with the treatment portion 9 shown in FIG. 2A.

Figure 4:
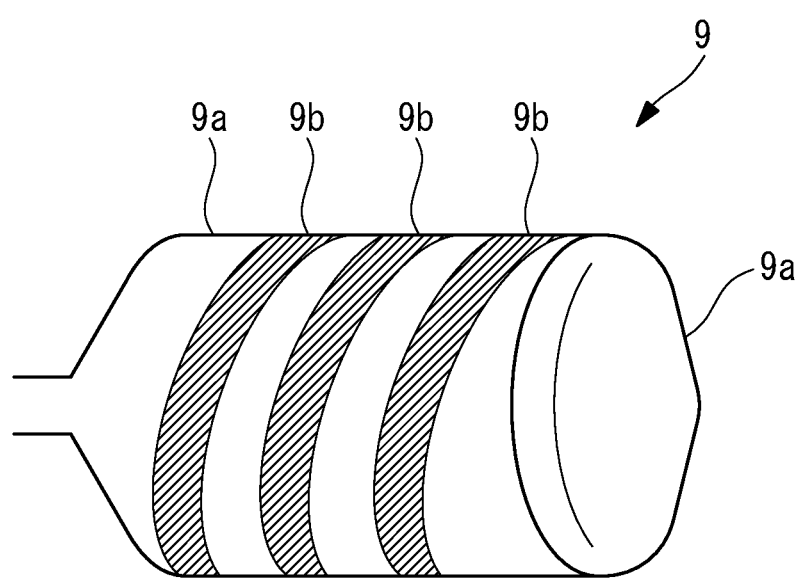
FIG. 4 is a view showing still another example configuration of the treatment portion shown in FIG. 1.

As shown in FIG. 4, the ablation part 9b may be formed in a spiral manner. In this case, the unit treatment area is obtained by multiplying the width of the ablation part 9b by the entire length thereof.

It is also possible to arrange ablation parts 9b in a grid manner or a spotted manner. In this case, the unit treatment area is the sum of the areas of the individual ablation parts 9b, which form the grid pattern or the spotted pattern.

The control device 7 includes an input unit 10, a target-value storage unit 11, the energy-source output unit 12, an area calculation unit 13, and a control unit 14.

An operator inputs, to the input unit 10, a target value for the total treatment area of the ileal mucosa to be treated by the ablation treatment tool 6. The target value input to the input unit 10 is stored in the target-value storage unit 11.

The target value for the total treatment area is set by the operator on the basis of at least one of the characteristics and the conditions of the patient.

The characteristics of the patient include, for example, age, height, weight, BMI (body-mass index), visceral fat mass, blood components (HbA1c, HDL, LDL, insulin, etc.), diabetes history, therapeutic drug history, history of insulin preparation use, and the length of intestinal tract that is measured on CT or MRI examination in advance.

The conditions of the patient include, for example: intestinal-bacteria composition analysis results; analysis results of the concentration and the composition of bile acids in blood or feces; evaluation results of bile-acid absorption disorder from a SeHCAT test; whether to promote new bile-acid synthesis or the results of improved carbohydrate metabolism, at the time of administration of a bile-acid absorption inhibitor; and whether to promote new bile-acid synthesis or the results of improved carbohydrate metabolism, when a bile-acid suppressor is temporarily placed inside the ileum.

The energy-source output unit 12 is connected to the ablation treatment tool 6. The energy-source output unit 12 outputs and supplies the energy source, which causes the energy to be released from the ablation part 9b, to the ablation treatment tool 6. The type of energy source is designed in accordance with the type of the energy to be released from the ablation part 9b. The energy source is, for example, high-frequency current, radio-frequency current, laser light, ultrasound, or a high-temperature fluid. The timing of outputting the energy source from the energy-source output unit 12 is controlled when the operator operates a switch provided on the ablation treatment tool 6, for example.

The area calculation unit 13 includes a unit-treatment-area storage unit 13a that stores the unit treatment area of the treatment portion 9 and a count unit 13b that counts the number of times the ablation treatment of the ileal mucosa is performed by the treatment portion 9.

The count unit 13b counts the number of times the energy source is output from the energy-source output unit 12, as the number of ablation treatments. Every time the count number in the count unit 13b is incremented, the area calculation unit 13 calculates the total treatment area by multiplying the unit treatment area by the count number. The total treatment area is the total of the areas of treatment regions on which the ablation treatment has been performed by the treatment portion 9. The area calculation unit 13 outputs the calculated total treatment area to the control unit 14.

The control unit 14 controls the termination of the ablation treatment performed by the treatment portion 9, on the basis of the total treatment area calculated by the area calculation unit 13. Specifically, every time the total treatment area is input from the area calculation unit 13, the control unit 14 compares the total treatment area with the target value, which is stored in the target-value storage unit 11. If the total treatment area is less than the target value, the control unit 14 allows the output of the energy source from the energy-source output unit 12. If the total treatment area is equal to or greater than the target value, the control unit 14 stops the output of the energy source from the energy-source output unit 12 and displays, on the display device 3, a notification of the termination of the ablation treatment.

Next, the ileal-mucosa ablation treatment method using the ablation system 100 will be described below.

Figure 5:
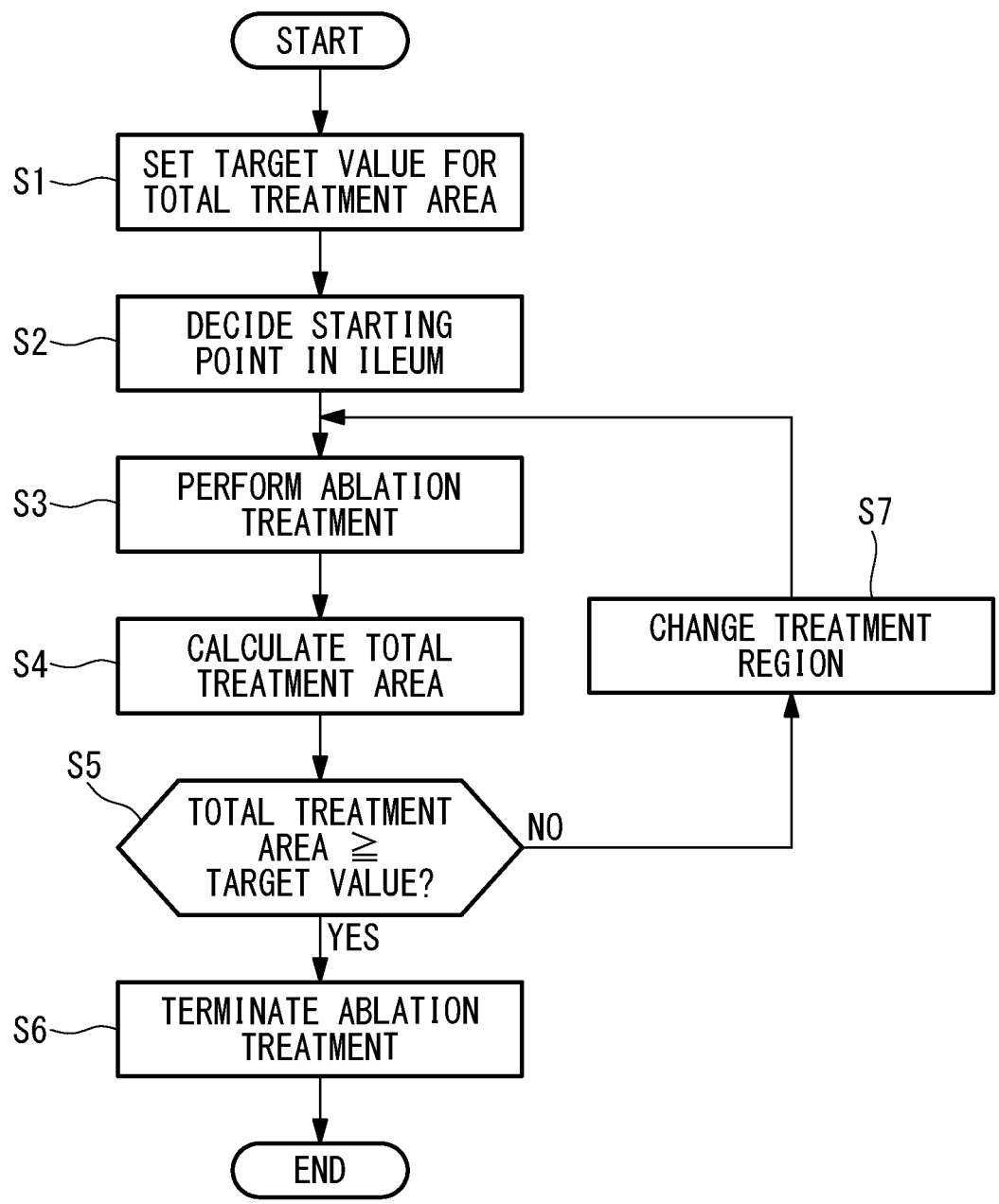
FIG. 5 is a flowchart showing an ileal-mucosa ablation treatment method according to one embodiment of the present invention.

As shown in FIG. 5, the ablation treatment method of this embodiment includes a target-value setting step S1 of setting a target value for the total treatment area of the ileal mucosa, a starting-point decision step S2 of deciding a starting point in the ileum, a treatment execution step S3 of performing the ablation treatment on the ileal mucosa, a total-treatment-area calculation step S4 of calculating the total treatment area of the ileal mucosa on which the ablation treatment has been performed, a determination step S5 of determining whether the total treatment area is equal to or greater than the target value, and a treatment termination step S6 of terminating the ablation treatment when the total treatment area becomes equal to or greater than the target value.

In the target-value setting step S1, the target value for the total treatment area is input to the input unit 10 by the operator and is stored in the target-value storage unit 11, thereby setting the target value in the control device 7 for the ablation treatment tool 6.

As described above, the target value is set on the basis of at least one of the characteristics and the conditions of the patient.

Figure 6A:
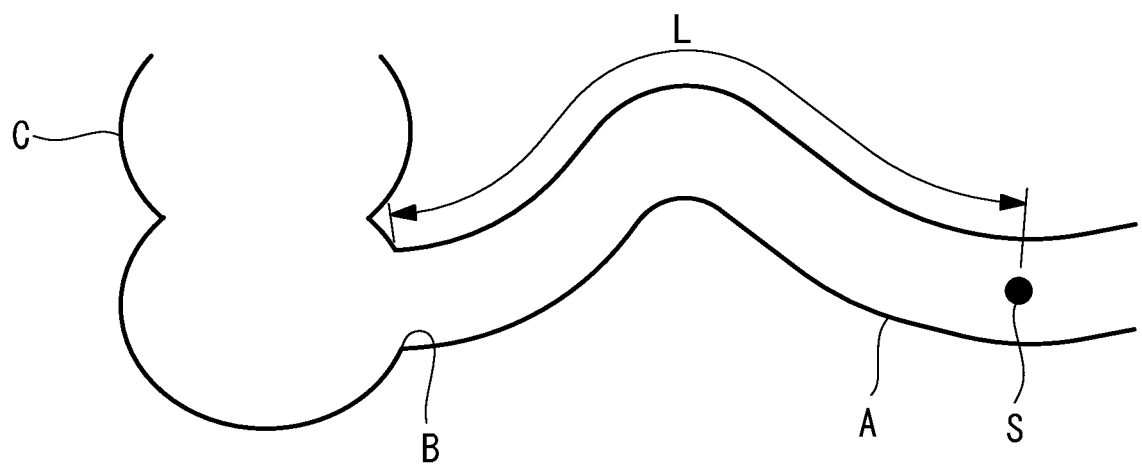
FIG. 6A is a view for explaining a step of deciding a starting point in the ileum.

In general, the overall length of the ileum is about 3 m. As shown in FIG. 6A, a bile-acid absorption region in the ileum A is located within a range of about 100 cm from the ileocecal valve B. The ileocecal valve B is a valve present at the terminal end of the ileum A, which is a connection section between the ileum A and the large intestine C, and is also called Bauhin's valve. Therefore, the target value for the total treatment area is set so as to be equal to or less than an area corresponding to 100 cm of the ileum A. In order to obtain an improvement effect on the metabolic diseases through the ileal-mucosa ablation treatment, it is inferred that about 10% suppression of the total bile-acid absorption amount in the ileum A is an appropriate amount. Therefore, a preferable range for the target value is an area corresponding to 10 cm to 40 cm of the ileum A.

Next, in the starting-point decision step S2, the starting point S is decided at the position a predetermined length L away from the ileocecal valve B toward the jejunum. If necessary, the decided starting point S may be marked by pigment or the like.

The starting point S is decided on the basis of information on an insertion distance of the endoscope 4 inserted into the ileum A. The endoscope 4 is inserted into the ileum A from the anus through the large intestine C, before or after Step S1. For example, the starting point S is decided within a range of about 100 cm from the ileocecal valve B, on the basis of an insertion length of the endoscope 4 inserted from the ileocecal valve B. The endoscope 4 may also be inserted into the ileum A from the mouth through the duodenum, before or after Step S1. In this case, the starting point S is decided within a range of about 100 cm from the ileocecal valve B, on the basis of a pullback length of the endoscope 4 pulled back from the ileocecal valve B after the endoscope 4 is made to reach the terminal end of the ileum A.

The starting point S may also be decided on the basis of an endoscopic image of the inside of the small intestine acquired by the endoscope 4. The frequency of circular folds in the ileum A is lower than the frequency of circular folds in the jejunum. Therefore, it is possible to decide the starting point S in the ileum A by distinguishing between the ileum A and the jejunum on the basis of the frequency of circular folds in the endoscopic image.

Figure 6B:
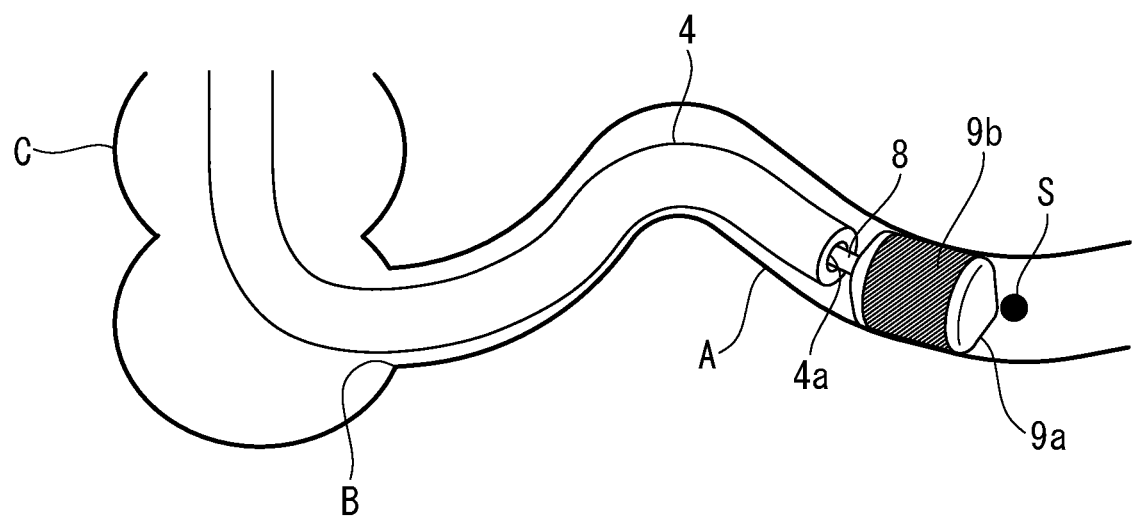
FIG. 6B is a view for explaining a step of performing ablation treatment on the ileal mucosa.

Next, in the treatment execution step S3, the ablation treatment is performed on the ileal mucosa by the treatment portion 9 of the ablation treatment tool 6. Specifically, as shown in FIG. 6B, the ablation treatment tool 6 is inserted into the ileum A through the treatment-tool channel 4a of the endoscope 4, the treatment portion 9 is positioned in the vicinity of the starting point S, the balloon 9a is made to expand, and the energy source is supplied from the energy-source output unit 12 of the control device 7 to the ablation treatment tool 6. Accordingly, the ablation treatment is performed on the unit treatment area of the ileal mucosa.

Next, in the total-treatment-area calculation step S4, the total treatment area of the ileal mucosa on which the ablation treatment has so far been performed by the treatment portion 9 is calculated by the area calculation unit 13. Specifically, the total treatment area is calculated by multiplying the unit treatment area of the treatment portion 9 by the number of times the energy source is output from the energy-source output unit 12.

Next, in the determination step S5, the control unit 14 determines whether the total treatment area is equal to or greater than the target value, which has been set in the target-value setting step S1.

If the total treatment area is equal to or greater than the target value (YES in Step S5), the flow advances to the treatment termination step S6. In the treatment termination step S6, the control unit 14 stops the output of the energy source from the energy-source output unit 12 and displays, on the display device 3, a notification of the termination of the ablation treatment. The operator recognizes that the total treatment area has become equal to or greater than the target value, and the ablation treatment of the ileal mucosa has been terminated, on the basis of the notification displayed on the display device 3, and stops the ablation treatment of the ileal mucosa.

On the other hand, if the total treatment area is less than the target value (NO in Step S5), the control unit 14 again allows the output of the energy source from the energy-source output unit 12. The operator changes, through movement of the treatment portion 9 inside the ileum A, the treatment region of the treatment portion 9 to a treatment region on which the ablation treatment has not yet been performed (Step S7), and performs the treatment execution step S3 again. The change in the treatment region and the ablation treatment are repeated until the total treatment area becomes equal to or greater than the target value.

Figure 7A:
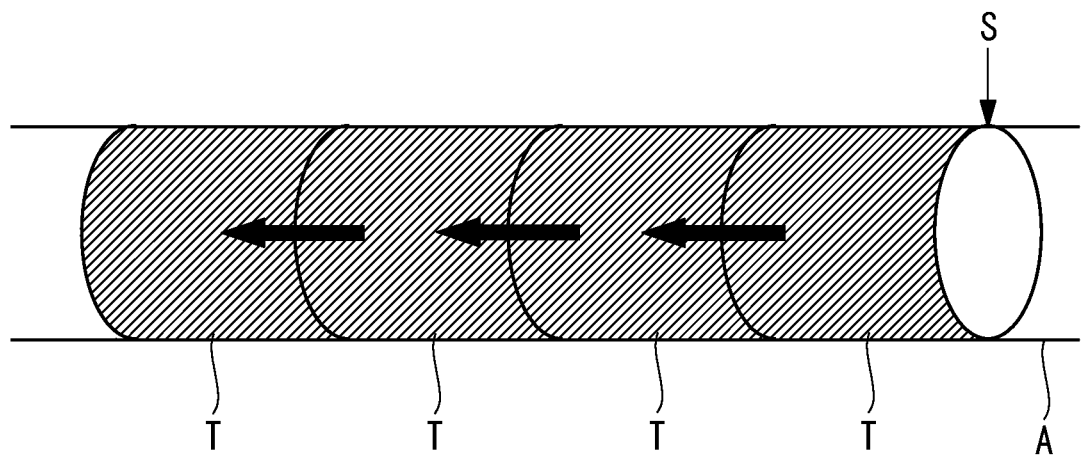
FIG. 7A is a view showing an example ablation pattern of the treatment portion shown in FIG. 2A.
Figure 7B:
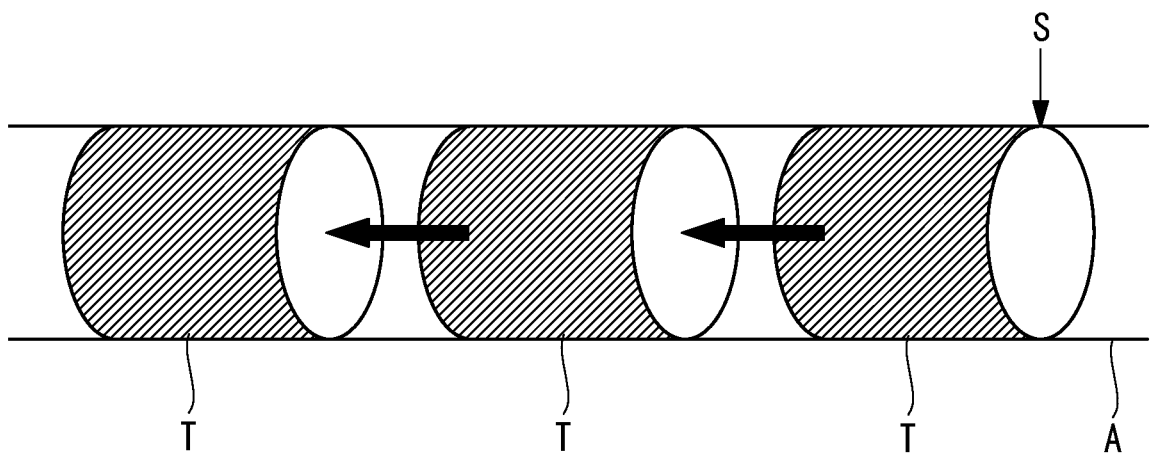
FIG. 7B is a view showing another example ablation pattern of the treatment portion shown in FIG. 2A.

In a case in which the endoscope 4 has been inserted into the ileum A from the anus through the large intestine C, in Step S7, the operator changes a treatment region T from the starting point S toward the ileocecal valve B (toward the left in FIGS. 7A and 7B), as shown in FIGS. 7A and 7B. Accordingly, the treatment region on which the ablation treatment is performed can be limited to the bile-acid absorption region between the starting point S and the ileocecal valve B. It is possible to prevent a situation in which the endoscope 4 comes in contact with a region on which the treatment has already been performed, thereby affecting tissues. The treatment regions T may be arranged with no gaps therebetween, as shown in FIG. 7A, or may be arranged with gaps therebetween, as shown in FIG. 7B. However, the positions of the treatment regions T are decided such that adjacent treatment regions T do not overlap with each other.

In a case in which the endoscope 4 has been inserted into the ileum A from the mouth through the duodenum, in Step S7, the operator changes the treatment region T from the starting point S toward the direction away from the ileocecal valve B (toward the right in FIGS. 7A and 7B), i.e., toward the jejunum. Accordingly, the same advantageous effect as described above can be obtained.

Here, a description will be given of the relationship between the bile-acid absorption suppression and metabolic diseases.

Some of the bile acids are newly synthesized in the liver from cholesterol, and most of the bile acids are reused through enterohepatic circulation. The enterohepatic circulation is a cycle in which the bile acids secreted from the liver to the duodenum via the bile duct are returned to the liver via the jejunum, the ileum, and the portal vein. It is known that the bile acids have a function of controlling the glucose metabolism in various organs in the process of the enterohepatic circulation. Specifically, the amount and the components of the bile acids are deeply involved in maintaining normal glucose metabolism. It is considered that adjustment of absorption of the bile acids into the blood vessel in the ileum is effective in order to adjust the amount and the components of the bile acids.

The ASBT (apical sodium-dependent bile acid transporter) present in the epithelium of the ileal mucosa plays a role in absorption of the bile acids in the ileum. It is known that partial resection of the ileum promotes the discharge of the bile acids to the large intestine, and the promotion of the discharge of the bile acids varies according to the length of the resection of the ileum. This is because a loss in the bile-acid absorption region reduces the bile-acid absorption efficiency. It is reported that, when a drug that inhibits absorption of the bile acids (ASBT inhibitor or bile-acid absorbent) is administered to a diabetic patient, the blood glucose level is reduced.

As a result of suppressing the absorption of the bile acids in the ileum through the partial resection of the ileum or by using a drug, discharge of the bile acids to the large intestine is promoted, thus reducing the amount of bile acids to be reused. The reduction in the bile acids is made up for by new synthesis of bile acids in the liver. The components of bile acids that are reused through the enterohepatic circulation differ from the components of bile acids that are newly synthesized in the liver. Therefore, when the absorption of bile acids is suppressed, the composition of bile acids (the ratio of the amount of bile acids reused to the amount of bile acids newly synthesized) changes. It is considered that improvement of diabetes through bile-acid absorption suppression is brought about by adjustment of the composition of bile acids. This matches the idea in which an improvement effect on obesity-complicated type 2 diabetes through surgical bypass surgery is brought about by adjustment of a bile-acid channel.

As in partial resection of the ileum and inhibition of bile-acid absorption by using a drug, the function of the ASBT is suppressed through the ablation treatment of the ileal mucosa, thereby suppressing the bile-acid absorption in the ileum A to adjust the composition of the bile acids, thus obtaining an improvement effect on diabetes. The level of the bile-acid absorption suppression and the composition of the bile acids are controlled by the total treatment area of the ileum A.

According to this embodiment, the total treatment area is calculated every time the ablation treatment is performed on the ileal mucosa, and the ablation treatment is terminated when the total treatment area becomes equal to or greater than the target value. Accordingly, there is an advantage in that the total treatment area of the ileal mucosa can be controlled to an appropriate area according to the characteristics and the conditions of the patient, thus making it possible to reliably show a desired treatment effect.

In this embodiment, it is preferred that the treatment depth of the ileal mucosa in the treatment execution step S3 be about 50 μm. The treatment depth is a depth from the surface of the ileal mucosa, in which the epithelial cells of the ileal mucosa are invaded through the ablation treatment. It is preferred that the treatment depth be a depth up to the underlying tissue of the ileal mucosa and a depth that does not reach a muscle layer.

Depending on the treatment depth, it is possible to control a period until the regeneration of the epithelial tissue of the ileal mucosa and to control whether the function of the epithelial tissue is reversibly impaired or is irreversibly impaired. Therefore, a remission period in which the treatment effect obtained through the ablation treatment is maintained can be controlled depending on the treatment depth.

In this embodiment, although the treatment portion 9 includes the balloon 9a and the ablation part 9b, which extends over the entire circumference of the balloon 9a, the form of the treatment portion 9 can be appropriately modified. FIGS. 8A to 8D show modifications of the treatment portion 9.

Figure 8A:
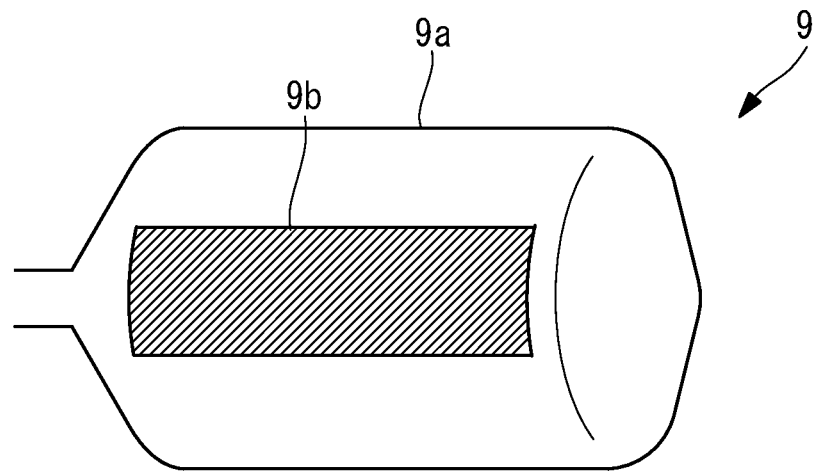
FIG. 8A is a view showing a modification of the treatment portion of the ablation treatment tool shown in FIG. 1.

A treatment portion 9 shown in FIG. 8A includes an ablation part 9b that is provided on a section of the balloon 9a in the circumferential direction. This ablation part 9b is suitable for being used to perform the ablation treatment only on a section of the ileal mucosa in the circumferential direction.

Figure 8B:
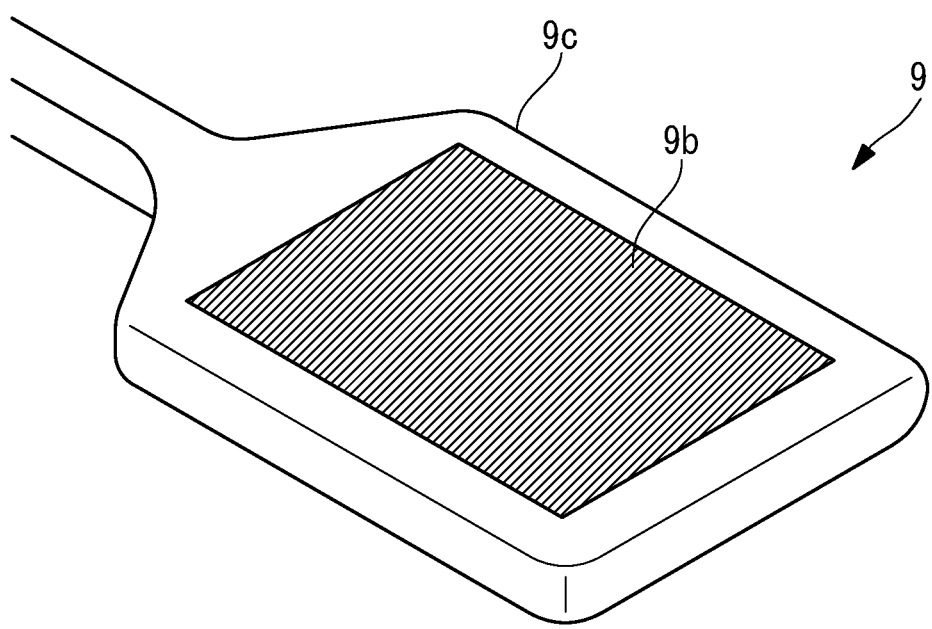
FIG. 8B is a view showing another modification of the treatment portion of the ablation treatment tool shown in FIG. 1.
Figure 8C:
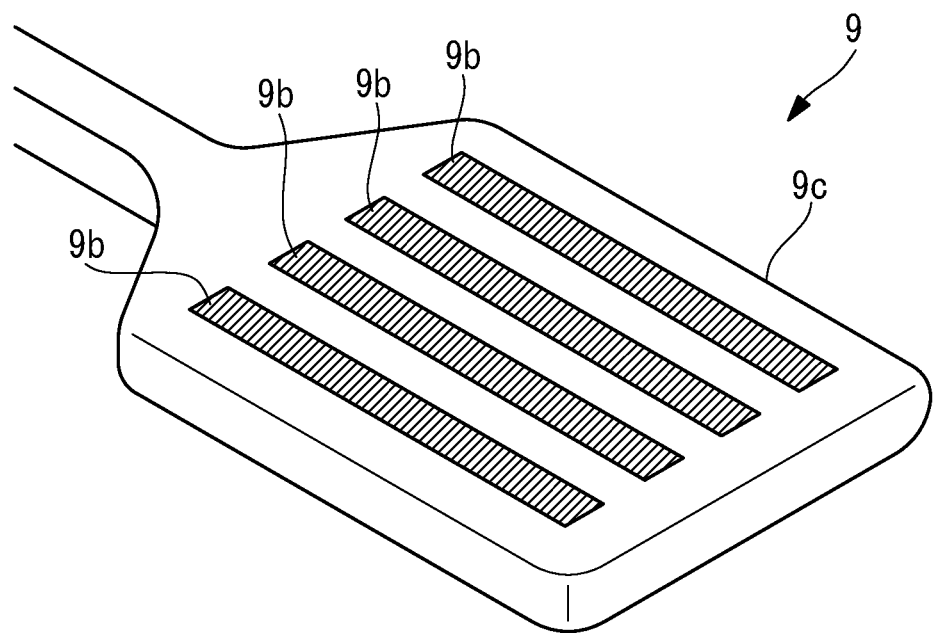
FIG. 8C is a view showing still another modification of the treatment portion of the ablation treatment tool shown in FIG. 1.

A treatment portion 9 shown in FIGS. 8B and 8C includes a plate 9c instead of the balloon 9a. A single ablation part 9b that has a wide area may be provided, as shown in FIG. 8B, or a plurality of ablation parts 9b that each have a small area may be provided at intervals, as shown in FIG. 8C.

Figure 8D:
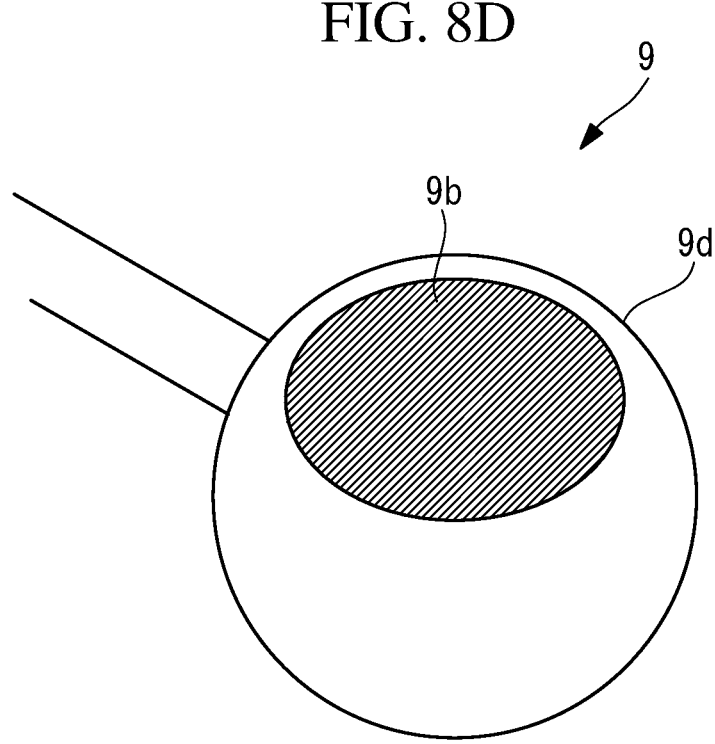
FIG. 8D is a view showing still another modification of the treatment portion of the ablation treatment tool shown in FIG. 1.

A treatment portion 9 shown in FIG. 8D includes a sphere 9d instead of the balloon 9a.

The shapes of the ablation parts 9b shown in FIGS. 8A to 8D are examples, and it is also possible to use an ablation part 9b that has another arbitrary shape. The unit treatment area of each of the treatment portions 9 that are shown in FIGS. 8A to 8D is the total area of the outer surface(s) of the ablation part(s) 9b, as in each of the treatment portions 9 that are shown in FIGS. 2A, 3A, and 4.

In this embodiment, although the ablation part 9b is directly brought into contact with the ileal mucosa, and the ablation treatment is performed on the contact region with the ablation part 9b, instead of this, it is also possible to perform the ablation treatment on the ileal mucosa without contact with the treatment portion 9. For example, the treatment portion 9 may be disposed at a position away from the ileal mucosa, and laser light or argon plasma may be radiated from the treatment portion 9 onto the ileal mucosa. In this case, laser light or argon plasma is radiated onto the ileal mucosa while maintaining a constant position of the treatment portion 9 with respect to the ileal mucosa, thereby making it possible to fix the unit treatment area per single ablation treatment.

In this embodiment, although the method for thermally degenerating the epithelial cells has been described as an ablation treatment method, instead of this, it is also possible to degenerate the epithelial cells or to remove the epithelial cells from the ileal mucosa by means other than heat, as long as the unit treatment area per single ablation treatment is fixed.

As another means for degenerating the epithelial cells, it is possible to adopt a method for cooling the ileal mucosa through cryoablation or a method for applying, to the ileal mucosa, a drug that chemically degenerates the epithelial cells.

As a means for removing the epithelial cells, it is possible to adopt a method for mechanically scraping off the ileal mucosa by using a brush, blade, knife, or the like.

In this embodiment, although the control unit 14 displays a notification on the display device 3, thereby notifying the operator of the termination of the ablation treatment in an area that is equal to or greater than the target value, it is also possible to notify the operator of the termination of the ablation treatment by another means, such as sound.

The control unit 14 may perform only one of the stoppage of the output of the energy source from the energy-source output unit 12 and the notification to the operator of the termination of the ablation treatment.

Second Embodiment

Next, an ablation system 200 and an ablation treatment method according to a second embodiment of the present invention will be described below with reference to the drawings.

In this embodiment, configurations different from those in the first embodiment will be described, identical reference signs are assigned to configurations common to those in the first embodiment, and a description thereof will be omitted.

Figure 9:
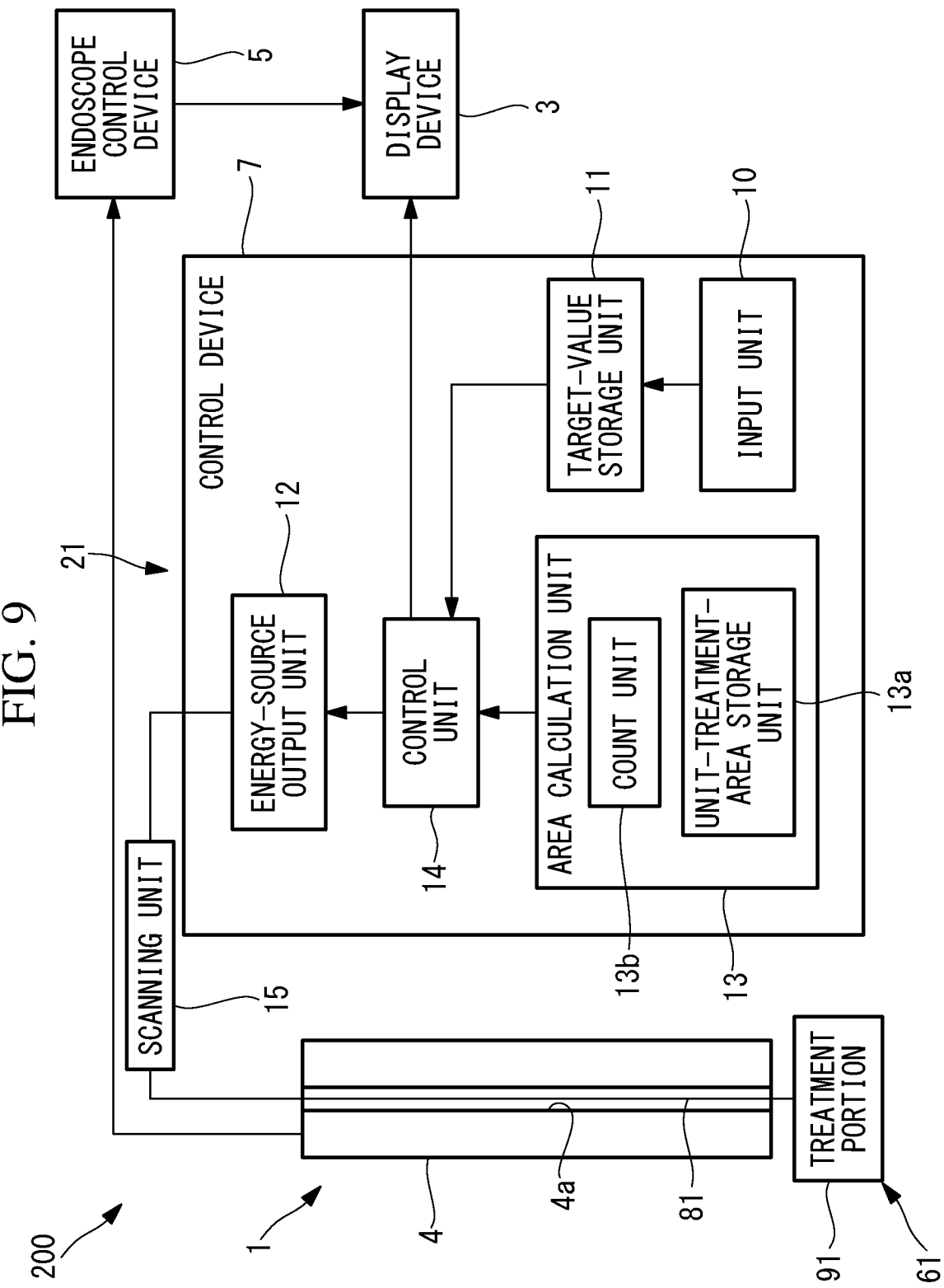
FIG. 9 is a diagram showing the overall configuration of an ablation system according to a second embodiment of the present invention.

As shown in FIG. 9, the ablation system 200 includes the endoscope device 1, an ablation-treatment device 21, and the display device 3.

The ablation-treatment device 21 includes an ablation treatment tool 61 and a control device 7 that controls the ablation treatment tool 61.

Figure 10A:
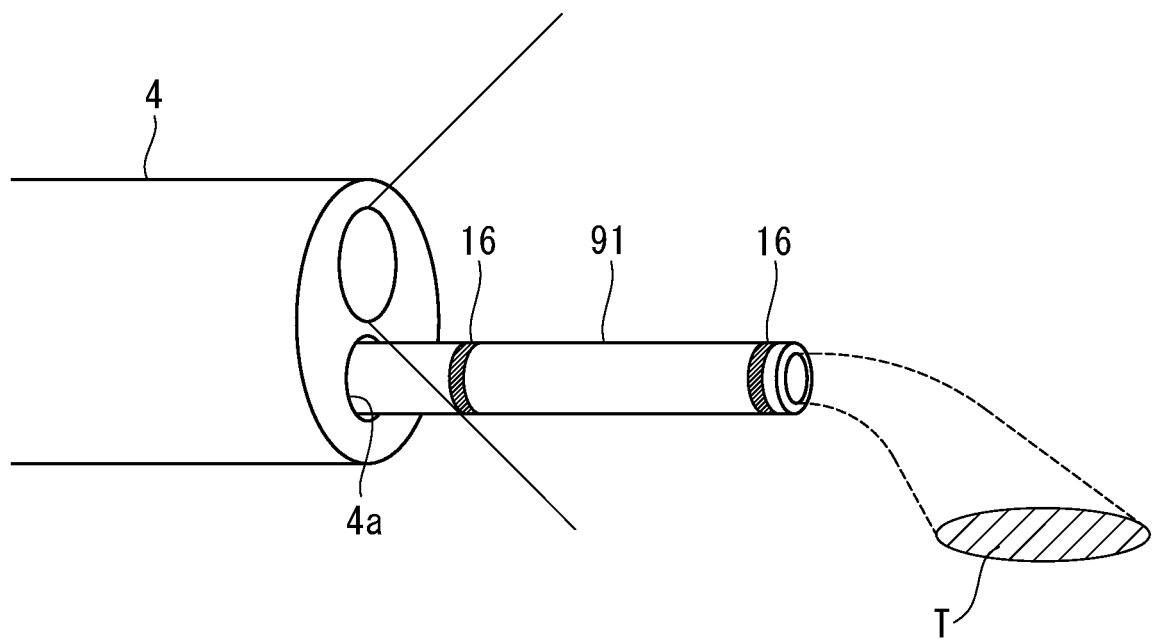
FIG. 10A is a view showing an example configuration of a treatment portion shown in FIG. 9.

The ablation treatment tool 61 includes a long flexible insertion portion 81 that can be inserted through the treatment-tool channel 4a and a treatment portion 91 that is provided at a distal end of the insertion portion 81. As shown in FIG. 10A, the treatment portion 91 emits argon plasma or laser light from a distal end. The argon plasma or laser light emitted from the treatment portion 91 is radiated onto the ileal mucosa around the treatment portion 91, to degenerate the epithelial cells of the ileal mucosa through argon-plasma coagulation or laser-light coagulation.

Figure 10B:
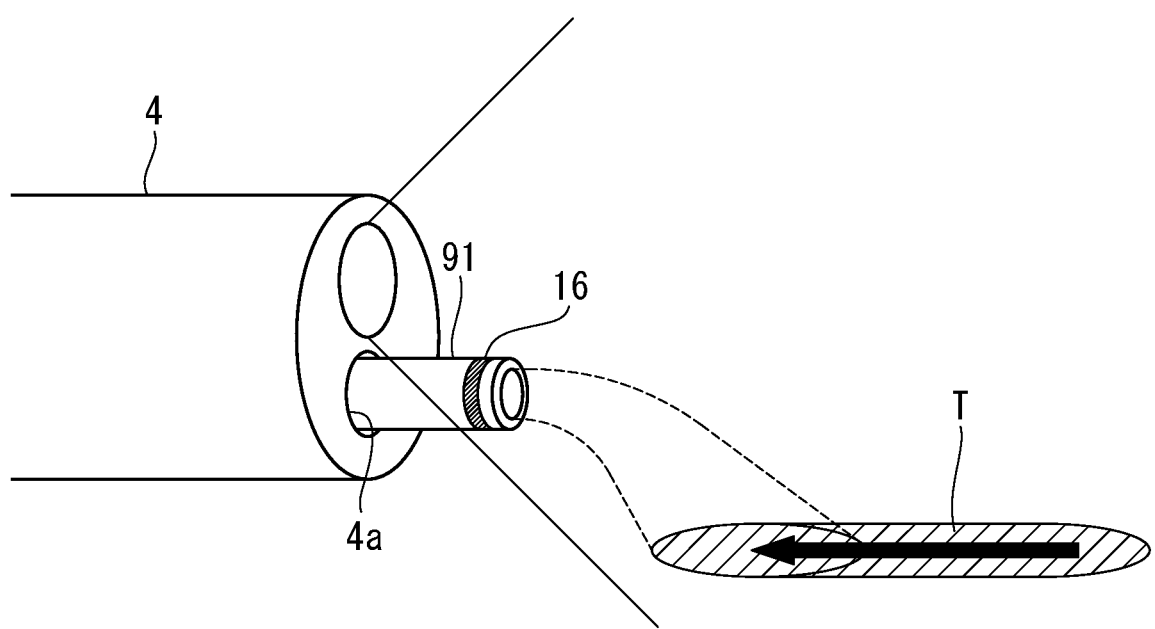
FIG. 10B is a view showing the operation of the treatment portion shown in FIG. 10A.

The ablation treatment tool 61 further includes a scanning unit 15 that moves the insertion portion 81 in the treatment-tool channel 4a toward the base end in the longitudinal direction with respect to the endoscope 4. As shown in FIG. 10B, the scanning unit 15 moves the treatment portion 91 through the movement of the insertion portion 81 in the longitudinal direction. Accordingly, an irradiation region irradiated with the argon plasma or laser light is scanned, from a position away from a distal end of the endoscope 4, in such a direction as to approach the distal end of the endoscope 4. The treatment region T is the total region irradiated with the argon plasma or laser light and is a long and narrow region extending in the longitudinal direction of the ileum A.

The ablation treatment tool 61 further includes a moving-amount control means for controlling the movement distance of the treatment portion 91 moved by the scanning unit 15, to a predetermined distance. The moving-amount control means is, for example, a pair of marks 16 provided at a distal-end section of the insertion portion 81, as shown in FIG. 10A. The marks 16, which form the pair, are provided at positions with a gap therebetween in the longitudinal direction of the insertion portion 81.

As shown in FIG. 10A, the treatment portion 91 is disposed at such a position that both marks 16 are observed in an endoscopic image. Then, as shown in FIG. 10B, the treatment portion 91 is moved toward the base end until the mark 16 that is close to the distal end reaches a predetermined position in the endoscopic image. Accordingly, the movement distance of the treatment portion 91 is controlled to the predetermined distance, thus making it possible to approximately fix the unit treatment area per single ablation treatment.

In this embodiment, variations in the unit treatment area per single ablation treatment can occur. Therefore, the average value of the unit treatment area may be measured in advance, and the average value of the unit treatment area may be used to calculate the total treatment area.

Next, the ileal-mucosa ablation treatment method using the ablation system 200 will be described below.

The ablation treatment method of this embodiment differs from the ablation treatment method of the first embodiment in terms of the treatment execution step S3. The other steps S1, S2, S4 to S7 are the same as those in the first embodiment.

In the treatment execution step S3, as shown in FIG. 10A, the ablation treatment tool 61 is inserted into the ileum A through the treatment-tool channel 4a of the endoscope 4, the treatment portion 91 is positioned in the vicinity of the starting point S, and the energy source is supplied from the energy-source output unit 12 of the control device 7 to the ablation treatment tool 61. Accordingly, argon plasma or laser light is radiated from the treatment portion 91 onto the ileal mucosa.

In a state in which the argon plasma or laser light is being emitted from the treatment portion 91, the operator moves, through operation of the scanning unit 15, the insertion portion 81 toward the base end by a predetermined amount, thereby scanning the irradiation region, which is irradiated with the argon plasma or laser light, on the ileal mucosa by the predetermined distance. After the irradiation region is scanned by the predetermined distance, the emission of the argon plasma or laser light from the treatment portion 91 is stopped. Accordingly, the ablation treatment is performed on the unit treatment area of the ileal mucosa.

In this way, according to this embodiment, the unit treatment area per single ablation treatment is decided through the movement of the treatment portion 91. The movement direction and the movement distance of the treatment portion 91 are controlled so as to be constant by using the scanning unit 15 and the moving-amount control means (marks 16), thereby making it possible to approximately fix the unit treatment area. Accordingly, as in the first embodiment, the total treatment area can be calculated from the unit treatment area and the number of ablation treatments.

Because the other advantageous effects of this embodiment are the same as those in the first embodiment, a description thereof will be omitted.

In this embodiment, although the treatment portion 91 performs the ablation treatment on the ileal mucosa by using argon plasma or laser light without contact, instead of this, it is also possible to adopt a contact-type treatment portion.

Figure 11:
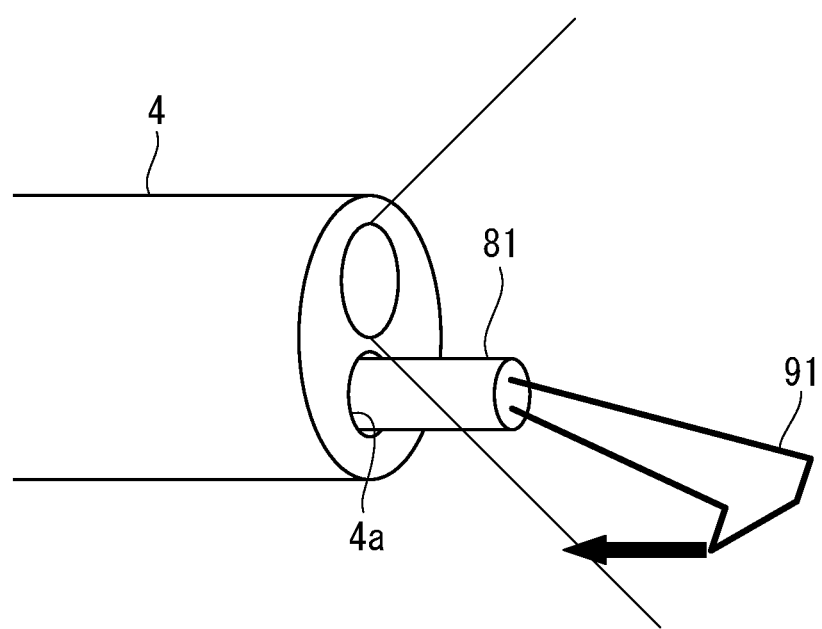
FIG. 11 is a view showing a modification of the treatment portion of an ablation treatment tool shown in FIG. 9.

For example, as shown in FIG. 11, the treatment portion 91 may be an electrode that releases energy. Alternatively, the treatment portion 91 may have an ablation part 9b that is brought into contact with the ileal mucosa, like the treatment portion 9 that is shown in FIGS. 8B and 8C.

Third Embodiment

Next, an ablation system 300 and an ablation treatment method according to a third embodiment of the present invention will be described below with reference to the drawings.

In this embodiment, configurations different from those in the first and second embodiments will be described, identical reference signs are assigned to configurations common to those in the first and second embodiments, and a description thereof will be omitted.

Figure 12:
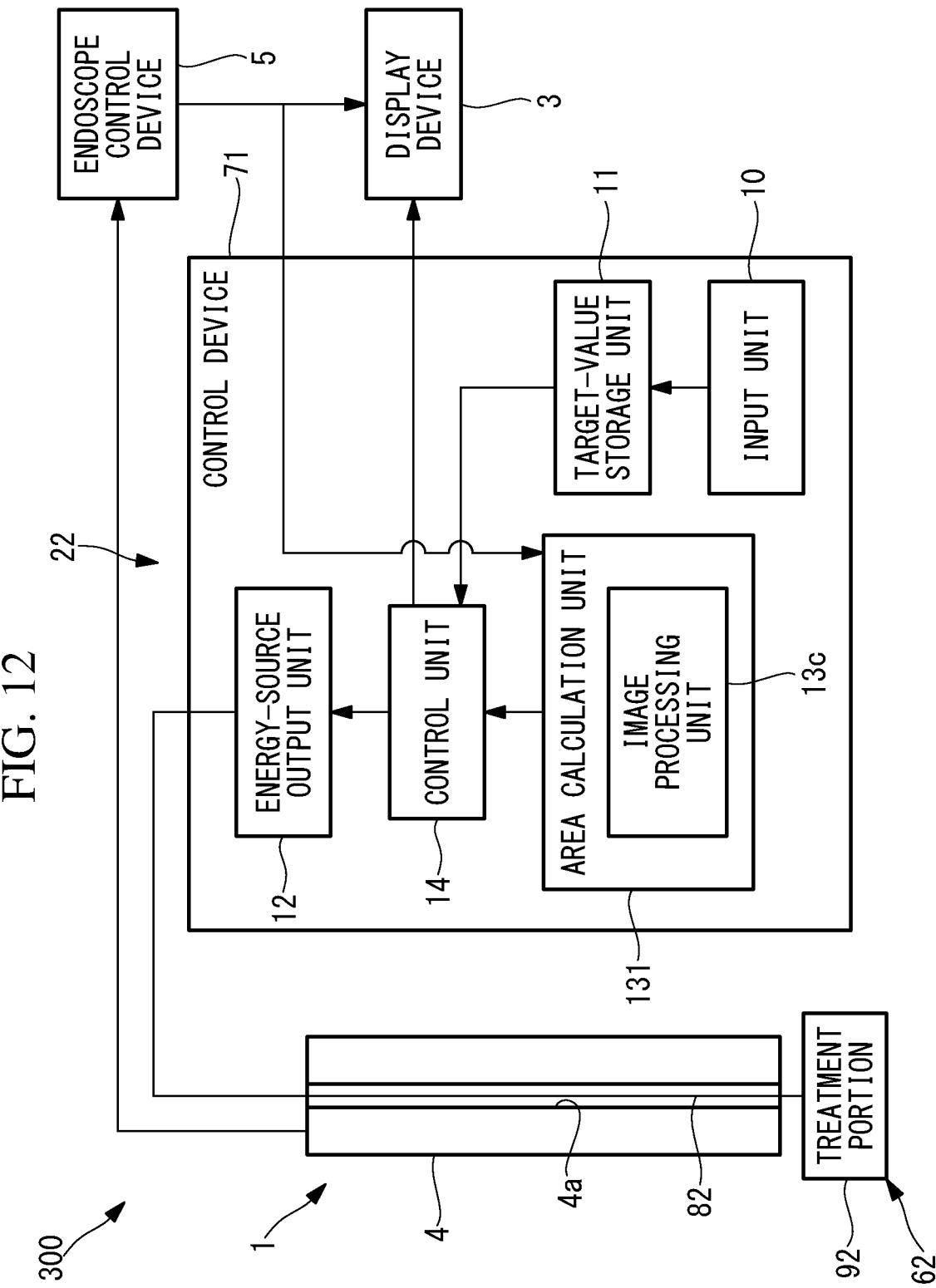
FIG. 12 is a diagram showing the overall configuration of an ablation system according to a third embodiment of the present invention.

As shown in FIG. 12, the ablation system 300 includes the endoscope device 1, an ablation-treatment device 22, and the display device 3.

The ablation-treatment device 22 includes an ablation treatment tool 62 and a control device 71 that controls the ablation treatment tool 62.

The ablation treatment tool 62 includes a long flexible insertion portion 82 that can be inserted through the treatment-tool channel 4a and a treatment portion 92 that is provided at a distal end of the insertion portion 82.

Figure 13:
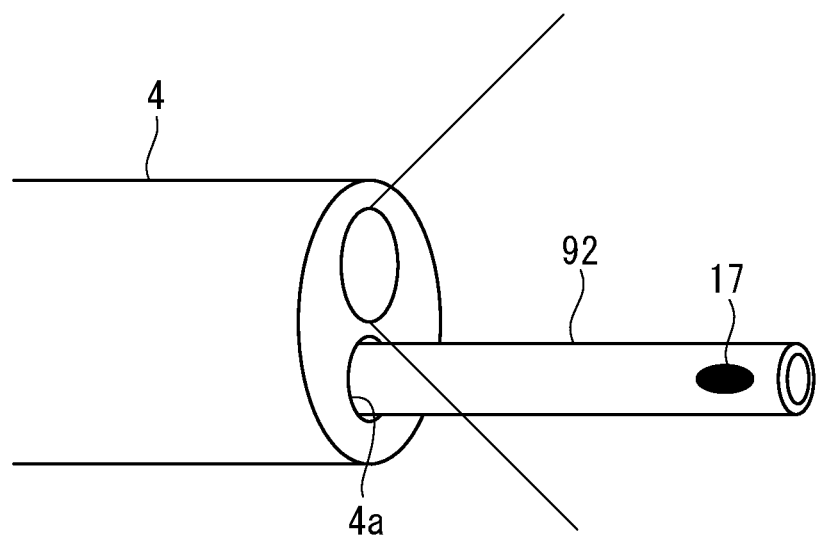
FIG. 13 is a view showing an example configuration of a treatment portion of an ablation treatment tool shown in FIG. 12.

As shown in FIG. 13, the treatment portion 92 has a size marker 17 provided thereon. The size marker 17 is provided at such a position as to be located within the field of view of the endoscope 4 when the treatment portion 92 performs the ablation treatment on the ileal mucosa. The other configurations of the treatment portion 92 are the same as those of the treatment portion 9 or the treatment portion 91.

The control device 71 includes the input unit 10, the target-value storage unit 11, the energy-source output unit 12, an area calculation unit 131, and the control unit 14.

The area calculation unit 131 includes an image processing unit 13c. The image processing unit 13c receives, from the endoscope control device 5, an endoscopic image acquired by the endoscope 4 and calculates the area of the individual treatment region T on the basis of the endoscopic image.

Figure 14:
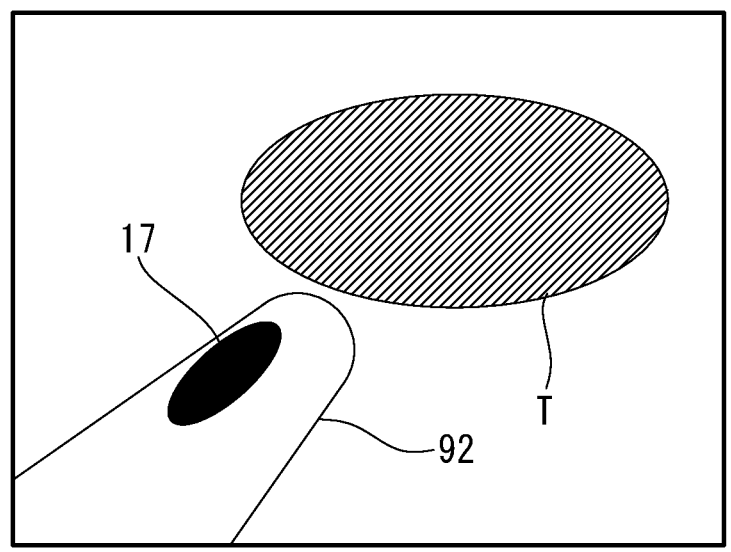
FIG. 14 is a view showing an example endoscopic image of a treatment region and the treatment portion in the ileum.

Specifically, as shown in FIG. 14, an endoscopic image acquired in the middle of or immediately after the ablation treatment contains the size marker 17 on the treatment portion 92 and the treatment region T on which the ablation treatment has been newly performed by the treatment portion 92. The treatment region T, in which the epithelial cells have been degenerated or removed through the ablation treatment, has a different color from normal ileal mucosa on which the ablation treatment has not been performed. Every time the energy source is output from the energy-source output unit 12, and the ablation treatment is performed on the ileum tissue by the treatment portion 92, the image processing unit 13c extracts the treatment region T from the endoscopic image on the basis of the color. The image processing unit 13c extracts the size marker 17 from the endoscopic image.

Next, the image processing unit 13c calculates the actual area of the treatment region T, from the ratio of the area of the extracted treatment region T to the area of the extracted size marker 17 and from the actual area of the size marker 17.

The area calculation unit 131 stores the area of the treatment region T calculated by the image processing unit 13c. Every time the area of the treatment region T is newly calculated by the image processing unit 13c, the area calculation unit 131 calculates the total treatment area by adding up the areas that have so far been calculated, and outputs the total treatment area to the control unit 14.

Next, the ileal-mucosa ablation treatment method using the ablation system 300 will be described below.

The ablation treatment method of this embodiment differs from the ablation treatment method of the first or second embodiment in terms of the total-treatment-area calculation step S4. The other steps S1 to S3 and S5 to S7 are the same as those in the first or second embodiment.

In the total-treatment-area calculation step S4, the area of the treatment region T on which the ablation treatment has been newly performed by the treatment portion 92 is calculated by the image processing unit 13c on the basis of the endoscopic image. Next, the total treatment area is calculated by adding up the areas of the treatment regions T that have so far been calculated. In order to more accurately calculate the actual area of the treatment region T, it is preferred that the size marker 17 be disposed as close to the treatment region T as possible.

In this way, according to this embodiment, every time the ablation treatment is performed, the area of the treatment region T is calculated one by one. For example, in a case in which the treatment portion 92 is a brush, blade, knife, or the like, and the operator manually operates the insertion portion 82 to move the treatment portion 92 for mechanically scraping off the ileal mucosa, it is difficult to make the area of the treatment region T constant. In a case in which the treatment portion 92 is the treatment portion 91 of the second embodiment, and the operator manually moves the insertion portion 82 in the longitudinal direction to scan the treatment region T by an arbitrary distance, the area of the treatment region T is not constant, either. In this way, even when the area of the treatment region T is not fixed, there is an advantage in that the total treatment area can be accurately calculated.

Because the other advantageous effects of this embodiment are the same as those in the first and second embodiments, a description thereof will be omitted.

In this embodiment, although the area of the treatment region T is calculated one by one every time the ablation treatment is performed, instead of this, it is also possible to acquire, after a plurality of ablation treatments, endoscopic images containing a plurality of treatment regions T by means of the endoscope 4 and to calculate the areas of the plurality of treatment regions T at the same time.

In the above-described first to third embodiments, although the control unit 14 terminates the ablation treatment when the total treatment area becomes equal to or greater than the target value, instead of this, the control unit 14 may terminate the ablation treatment when an area that is obtained by subtracting the target value from the sum of the total treatment area and the area of the next single treatment region becomes equal to or greater than an area equal to a predetermined ratio $\alpha$ ($0<\alpha<1$) of the area of the next single treatment region.

Figure 15A:
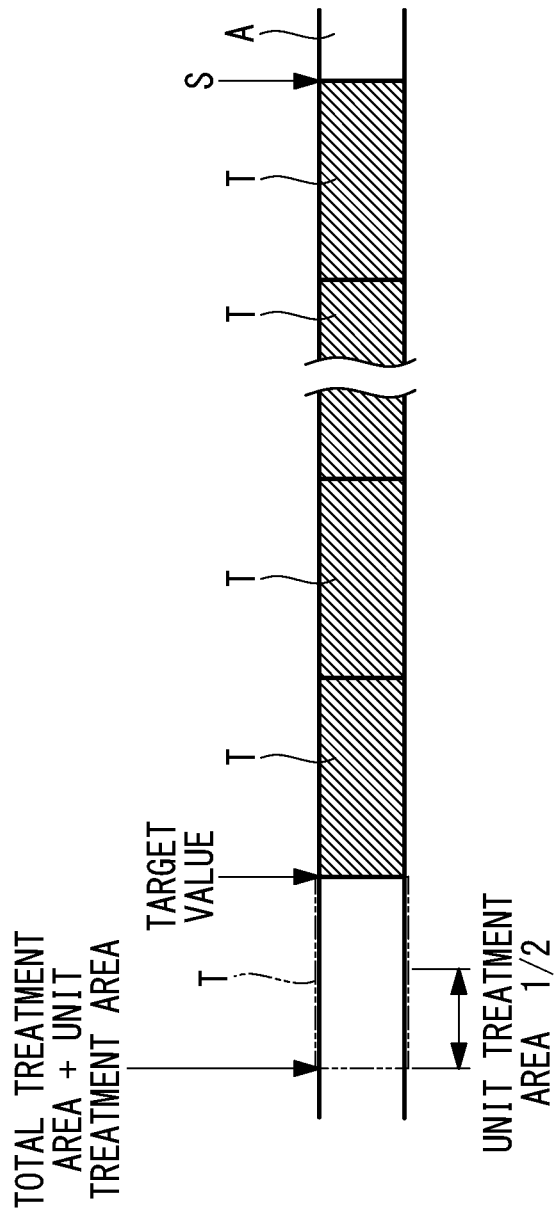
FIG. 15A is a view for explaining a modification of a determination step and a treatment termination step of the ileal-mucosa ablation treatment method shown in FIG. 5.
Figure 15B:
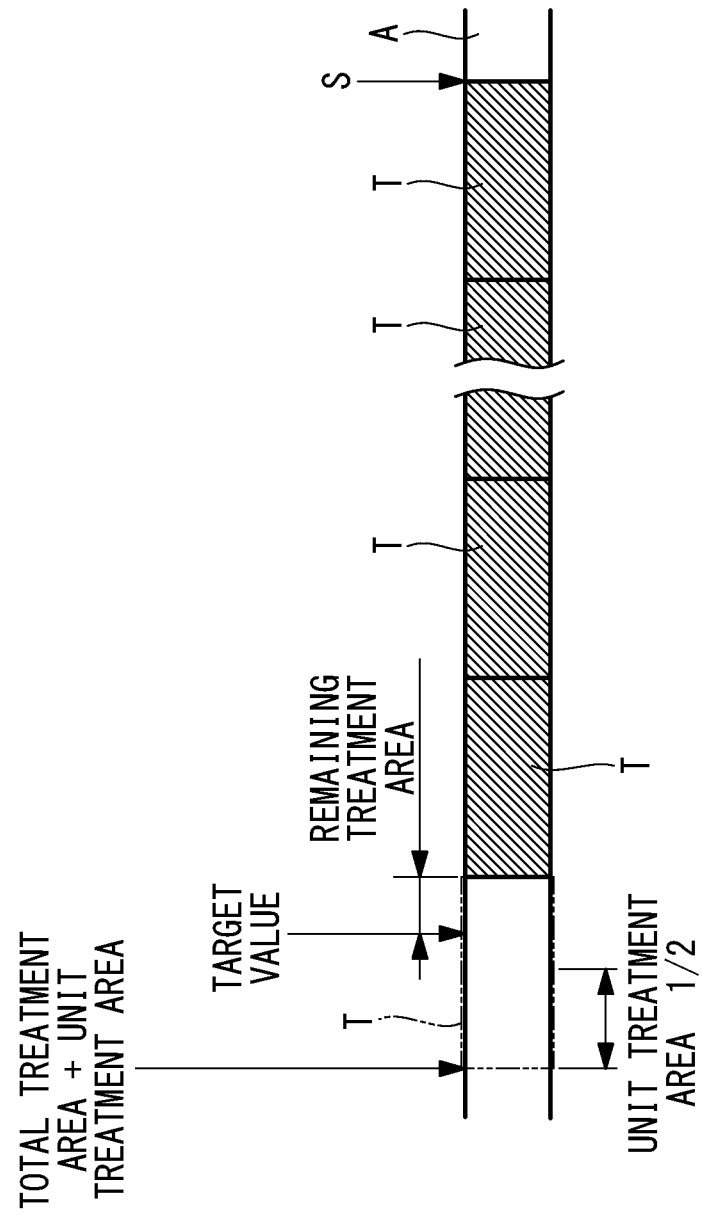
FIG. 15B is a view for explaining the modification of the determination step and the treatment termination step of the ileal-mucosa ablation treatment method shown in FIG. 5.
Figure 15C:
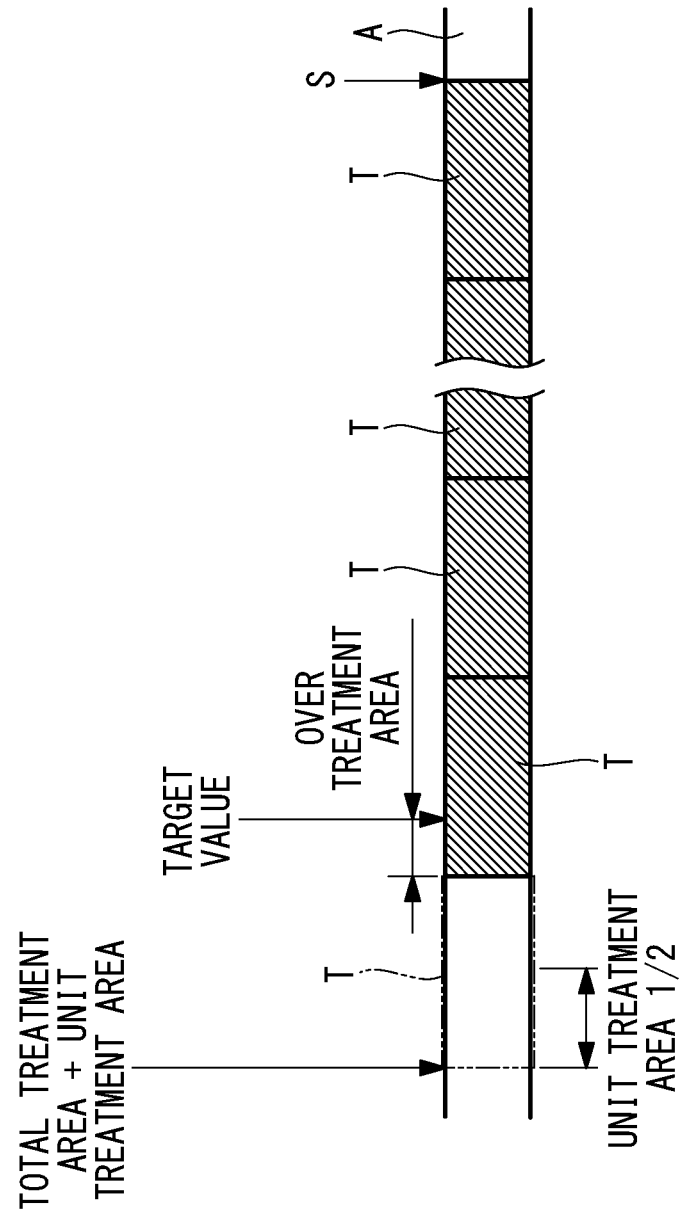
FIG. 15C is a view for explaining the modification of the determination step and the treatment termination step of the ileal-mucosa ablation treatment method shown in FIG. 5.

For example, as shown in FIG. 15A, when the total treatment area is equal to the target value, an area obtained by subtracting the target value from the sum of the total treatment area and the unit treatment area becomes greater than the area ($\alpha \times D$) equal to the predetermined ratio $\alpha$ of the unit treatment area D. In this case, the ablation treatment is terminated. In FIGS. 15A to 15C, although the predetermined ratio $\alpha$ is ½, the predetermined ratio $\alpha$ may be another value.

As shown in FIG. 15B, when the total treatment area is less than the target value, and the remaining treatment area (=the target value−the total treatment area) is less than the area $\alpha \times D$, the area obtained by subtracting the target value from the sum of the total treatment area and the unit treatment area becomes equal to or greater than the area $\alpha \times D$. In this case, the ablation treatment is terminated.

On the other hand, when the remaining treatment area (=the target value−the total treatment area) is equal to or greater than the area $\alpha \times D$, the area obtained by subtracting the target value from the sum of the total treatment area and the unit treatment area becomes less than the area $\alpha \times D$. In this case, the next single ablation treatment is performed. As a result of performing the next single ablation treatment, as shown in FIG. 15C, the total treatment area becomes greater than the target value, an over treatment area (=−(the target value−the total treatment area)) becomes less than the area $\alpha \times D$, and the area obtained by subtracting the target value from the sum of the total treatment area and the unit treatment area becomes equal to or greater than the area $\alpha \times D$. Therefore, the ablation treatment is terminated.

By controlling the termination of the ablation treatment in this way, the total treatment area of the ileal mucosa is controlled to an area equal to or approximately equal to the target value. Therefore, it is possible to reliably show a desired treatment effect.

In the above-described first to third embodiments, although metabolic diseases, such as diabetes, are illustrated as an application example of the ileal-mucosa ablation treatment method, the ileal-mucosa ablation treatment method of this embodiment can also be applied to treatment of other diseases, such as obesity, nonalcoholic steatohepatitis, nonalcoholic fatty liver disease, and inflammatory bowel disease.

As a result, the following aspect is read from the above described embodiment of the present invention.

In order to achieve the above-described object, the present invention provides the following solutions.

According to a first aspect, the present invention provides an ablation-treatment-tool control device that controls an ablation treatment tool that performs ablation treatment on ileal mucosa, which covers an inner surface of the ileum, the control device including: a target-value storage unit that stores a target value for the total treatment area of the ileal mucosa, the target value being set on the basis of at least one of the characteristics and the conditions of a patient; an energy-source output unit that outputs, to the ablation treatment tool, an energy source for performing the ablation treatment; an area calculation unit that calculates the total treatment area, which is the total of the areas of treatment regions of the ileal mucosa on which the ablation treatment has been performed by the ablation treatment tool; and a control unit that controls termination of the ablation treatment of the ileal mucosa performed by the ablation treatment tool, wherein the control unit notifies an operator of the termination of the ablation treatment or stops the output of the energy source from the energy-source output unit when the calculated total treatment area of the ileal mucosa becomes equal to or greater than the target value.

According to this aspect, the ablation treatment tool is connected to the energy-source output unit, and the energy source is supplied from the energy-source output unit to the ablation treatment tool disposed in the ileum, thereby making it possible to perform the ablation treatment on the ileal mucosa by means of the ablation treatment tool. Furthermore, the ablation treatment of the ileal mucosa is repeatedly performed while changing the treatment region, thereby making it possible to perform the ablation treatment on the ileal mucosa of an area required to show a treatment effect.

In this case, while the ablation treatment is repeatedly performed, the area calculation unit calculates the total treatment area of the ileal mucosa on which the ablation treatment has so far been performed. The target-value storage unit stores a target value for the total treatment area, the target value being set on the basis of at least one of the characteristics and the conditions of the patient. When the total treatment area calculated by the area calculation unit becomes equal to or greater than the target value, the control unit notifies an operator of termination of the ablation treatment or stops the output of the energy source from the energy-source output unit, thereby terminating the ablation treatment performed by the ablation treatment tool. Accordingly, it is possible to appropriately control the treatment area of the ileal mucosa and to reliably show a desired treatment effect.

According to a second aspect, the present invention provides an ablation-treatment-tool control device that controls an ablation treatment tool that performs ablation treatment on ileal mucosa, which covers an inner surface of the ileum, the control device including: a target-value storage unit that stores a target value for the total treatment area of the ileal mucosa, the target value being set on the basis of at least one of the characteristics and the conditions of a patient; an energy-source output unit that outputs, to the ablation treatment tool, an energy source for performing the ablation treatment; an area calculation unit that calculates the total treatment area, which is the total of the areas of treatment regions of the ileal mucosa on which the ablation treatment has been performed by the ablation treatment tool; and a control unit that controls termination of the ablation treatment of the ileal mucosa performed by the ablation treatment tool, wherein the control unit notifies an operator of the termination of the ablation treatment or stops the output of the energy source from the energy-source output unit when an area that is obtained by subtracting the target value from the sum of the calculated total treatment area of the ileal mucosa and the area of the next single treatment region becomes equal to or greater than an area equal to a predetermined ratio of the area of the next single treatment region.

According to this aspect, the ablation treatment tool is connected to the energy-source output unit, and the energy source is supplied from the energy-source output unit to the ablation treatment tool disposed in the ileum, thereby making it possible to perform the ablation treatment on the ileal mucosa by means of the ablation treatment tool. Furthermore, the ablation treatment of the ileal mucosa is repeatedly performed while changing the treatment region, thereby making it possible to perform the ablation treatment on the ileal mucosa of an area required to show a treatment effect.

In this case, while the ablation treatment is repeatedly performed, the area calculation unit calculates the total treatment area of the ileal mucosa on which the ablation treatment has so far been performed. The target-value storage unit stores a target value for the total treatment area, the target value being set on the basis of at least one of the characteristics and the conditions of the patient. When the area obtained by subtracting the target value from the sum of the total treatment area calculated by the area calculation unit and the area of the next single treatment region becomes an area equal to a predetermined ratio of the area of the next single treatment region, the control unit notifies an operator of termination of the ablation treatment or stops the output of the energy source from the energy-source output unit, thereby terminating the ablation treatment performed by the ablation treatment tool. Accordingly, it is possible to appropriately control the treatment area of the ileal mucosa and to reliably show a desired treatment effect.

In the first and second aspects, a unit treatment area, which is a treatment area of the ileal mucosa per single ablation treatment performed by the ablation treatment tool, may be fixed; and the area calculation unit may calculate the total treatment area by multiplying the unit treatment area by the number of times the energy source is output from the energy-source output unit.

When the unit treatment area is fixed, the total treatment area can be easily calculated with this configuration.

In the first and second aspects, the area calculation unit may receive an endoscopic image of the ileal mucosa from an endoscope, may calculate the area of a new treatment region every time the ablation treatment is performed on the ileal mucosa, on the basis of the endoscopic image, and may calculate the total treatment area by adding up the calculated areas of the treatment regions.

With this configuration, the area of the ileal mucosa on which the ablation treatment has actually been performed can be calculated on the basis of an endoscopic image. Therefore, even when the treatment area of the ileal mucosa per single ablation treatment is not fixed, the accurate total treatment area can be calculated.

According to a third aspect, the present invention provides an ablation system including: an ablation treatment tool; and one of the above-described control devices, which control the ablation treatment tool.

The third aspect may further include an endoscope that has a treatment-tool channel and that is inserted into the ileum, wherein the ablation treatment tool may be able to be inserted through the treatment-tool channel.

According to a fourth aspect, the present invention provides an ileal-mucosa ablation treatment method that is an ablation treatment method for ileal mucosa, which covers an inner surface of the ileum, the method including: a step of setting a target value for the total treatment area of the ileal mucosa, the target value being set on the basis of at least one of the characteristics and the conditions of a patient; a step of repeatedly performing ablation treatment on the ileal mucosa while changing a treatment region; a step of calculating the total treatment area, which is the total of the areas of treatment regions of the ileal mucosa on which the ablation treatment has been performed; and a step of terminating the ablation treatment when the calculated total treatment area of the ileal mucosa becomes equal to or greater than the target value.

According to this aspect, the ablation treatment of the ileal mucosa is repeatedly performed while changing the treatment region, thereby making it possible to perform the ablation treatment on the ileal mucosa of an area required to show a treatment effect.

In this case, while the ablation treatment is repeatedly performed, the total treatment area of the ileal mucosa is calculated. Then, when the calculated total treatment area becomes equal to or greater than the target value, which has been set on the basis of at least one the characteristics and the conditions of the patient, the ablation treatment is terminated. Accordingly, it is possible to appropriately control the treatment area of the ileal mucosa and to reliably show a desired treatment effect.

According to a fifth aspect, the present invention provides an ileal-mucosa ablation treatment method that is an ablation treatment method for ileal mucosa, which covers an inner surface of the ileum, the method including: a step of setting a target value for the total treatment area of the ileal mucosa, the target value being set on the basis of at least one of the characteristics and the conditions of a patient; a step of repeatedly performing ablation treatment on the ileal mucosa while changing a treatment region; a step of calculating the total treatment area, which is the total of the areas of treatment regions of the ileal mucosa on which the ablation treatment has been performed; and a step of terminating the ablation treatment when an area that is obtained by subtracting the target value from the sum of the calculated total treatment area of the ileal mucosa and the area of the next single treatment region becomes equal to or greater than an area equal to a predetermined ratio of the area of the next single treatment region.

According to this aspect, the ablation treatment of the ileal mucosa is repeatedly performed while changing the treatment region, thereby making it possible to perform the ablation treatment on the ileal mucosa of an area required to show a treatment effect.

In this case, while the ablation treatment is repeatedly performed, the total treatment area of the ileal mucosa is calculated. Then, when the area obtained by subtracting the target value from the sum of the calculated total treatment area and the area of the next single treatment region becomes an area equal to a predetermined ratio of the area of the next single treatment region, the ablation treatment is terminated. Accordingly, it is possible to appropriately control the treatment area of the ileal mucosa and to reliably show a desired treatment effect.

The above-described fourth and fifth aspects may further include a step of deciding a starting point at a position a predetermined length away from a terminal end of the ileum toward the jejunum, on the basis of information on an insertion distance of the endoscope inserted into the ileum from the large intestine or an endoscopic image acquired by the endoscope, wherein, in the step of repeatedly performing the ablation treatment, the treatment region may be changed from the starting point toward the terminal end of the ileum.

Because no clear boundary exists between the ileum and the jejunum, when the treatment region is changed from a section of the ileum close to the terminal end toward a section thereof close to the jejunum, the ablation treatment might be performed on the jejunal mucosa, not the ileal mucosa. The starting point is decided in the ileum, and the treatment region is changed from the starting point toward the terminal end of the ileum, thereby making it possible to reliably perform the ablation treatment on the ileal mucosa in the bile-acid absorption region. Furthermore, in a case in which the endoscope is inserted into the ileum from the anus through the large intestine, the treatment region is changed in the direction in which the endoscope is pulled back, thus making it possible to protect a region on which the treatment has already been performed, from contact with the endoscope.

The above-described fourth and fifth aspects may further include a step of deciding a starting point at a position a predetermined length away from a terminal end of the ileum toward the jejunum, on the basis of information on an insertion distance of the endoscope inserted into the ileum from the duodenum or an endoscopic image acquired by the endoscope, wherein, in the step of repeatedly performing the ablation treatment, the treatment region may be changed from the starting point toward the jejunum.

The starting point is decided in the ileum, and the treatment region is changed from the starting point toward the jejunum, thereby making it possible to reliably perform the ablation treatment on the ileal mucosa in the bile-acid absorption region. Furthermore, in a case in which the endoscope is inserted into the ileum from the mouth through the duodenum, the treatment region is changed in the direction in which the endoscope is pulled back, thus making it possible to protect a region on which the treatment has already been performed, from contact with the endoscope.

In the above-described fourth and fifth aspects, in the step of repeatedly performing the ablation treatment, a unit treatment area, which is a treatment area of the ileal mucosa per single ablation treatment, may be fixed; and, in the step of calculating the total treatment area of the ileal mucosa, the total treatment area may be calculated by multiplying the unit treatment area by the number of ablation treatments.

When the unit treatment area is fixed, the total treatment area can be easily calculated with this configuration.

In the above-described fourth and fifth aspects, in the step of calculating the total treatment area of the ileal mucosa, the total treatment area may be calculated by calculating the area of a new treatment region every time the ablation treatment is performed on the ileal mucosa, on the basis of an endoscopic image, and by adding up the areas of the calculated treatment regions.

With this configuration, the area of the ileal mucosa on which the ablation treatment has actually been performed can be calculated on the basis of an endoscopic image. Therefore, even when the treatment area of the ileal mucosa per single ablation treatment is not fixed, the accurate total treatment area can be calculated.

REFERENCE SIGNS LIST 1 endoscope device
2, 21, 22 ablation-treatment device
3 display device
4 endoscope
4a treatment-tool channel
5 endoscope control device
6, 61, 62 ablation treatment tool
7, 71 control device (ablation-treatment-tool control device)
8 insertion portion
9, 91, 92 treatment portion
9a balloon
9b ablation part
9c plate
10 input unit 11 target-value storage unit
12 energy-source output unit
13, 131 area calculation unit
14 control unit
15 scanning unit
16 mark
17 size marker
100, 200, 300 ablation system
A ileum
B ileocecal valve
C large intestine

The invention claimed is:

1. An ablation-treatment-tool control device for controlling an ablation treatment tool to perform ablation treatment on ileal mucosa, which covers an inner surface of an ileum, the ablation-treatment-tool control device comprising:
    a target-value storage unit configured to store a target value for a total treatment area of the ileal mucosa, the target value being set on the basis of at least one of characteristics and conditions of a patient;
    an energy-source output unit configured to output, to the ablation treatment tool, an energy source for performing the ablation treatment;
    an area calculation unit configured to calculate the total treatment area, which is a total of areas of treatment regions of the ileal mucosa on which the ablation treatment has been performed for at least two or more treatment regions by the ablation treatment tool; and
    a control unit configured to:
        determine whether the calculated total treatment area is equal to or greater than the target value; and
        in response to determining that the calculated total treatment area is equal to or greater than the target value, perform one or more of stop the output of the energy source from the energy-source output unit to terminate the ablation treatment and notify an operator of the termination of the ablation treatment.

2. The ablation-treatment-tool control device according to claim 1, wherein:
    a unit treatment area, which is a treatment area of the ileal mucosa per single ablation treatment performed by the ablation treatment tool, is fixed; and
    the area calculation unit is configured to calculate the total treatment area by multiplying the unit treatment area by a number of times the energy source is output from the energy-source output unit.

3. The ablation-treatment-tool control device according to claim 1, wherein the area calculation unit is configured to:
    receive an endoscopic image of the ileal mucosa from an endoscope;
    calculate an area of a new treatment region every time the ablation treatment is performed on the ileal mucosa, on the basis of the endoscopic image; and
    calculate the total treatment area by adding up the calculated areas of the treatment regions.

4. An ablation system comprising:
    an ablation treatment tool; and
    the ablation-treatment-tool control device according to claim 1, which is configured to control the ablation treatment tool.

5. The ablation system according to claim 4, further comprising an endoscope that has a treatment-tool channel and is configured to be inserted into the ileum, wherein the ablation treatment tool is configured to be inserted through the treatment-tool channel.

6. An ablation-treatment-tool control device for controlling an ablation treatment tool to perform ablation treatment on ileal mucosa, which covers an inner surface of an ileum, the ablation-treatment-tool control device comprising:
    a target-value storage unit configured to store a target value for a total treatment area of the ileal mucosa, the target value being set on the basis of at least one of characteristics and conditions of a patient;
    an energy-source output unit configured to output, to the ablation treatment tool, an energy source for performing the ablation treatment;
    an area calculation unit configured to calculate the total treatment area, which is a total of areas of treatment regions of the ileal mucosa on which the ablation treatment has been performed for at least two or more treatment regions by the ablation treatment tool; and
    a control unit configured to:
        determine whether an area that is obtained by subtracting the target value from a sum of the calculated total treatment area and an area of a next single treatment region is equal to or greater than an area equal to a predetermined ratio of the area of the next single treatment region; and
        in response to determining that the area that is obtained by subtracting the target value from the sum of the calculated total treatment area and the area of the next single treatment region is equal to or greater than the area equal to the predetermined ratio of the area of the next single treatment region, perform one or more of stop the output of the energy source from the energy-source output unit to terminate the ablation treatment and notify an operator of the termination of the ablation treatment.

7. The ablation-treatment-tool control device according to claim 6, wherein:
    a unit treatment area, which is a treatment area of the ileal mucosa per single ablation treatment performed by the ablation treatment tool, is fixed; and
    the area calculation unit is configured to calculate the total treatment area by multiplying the unit treatment area by a number of times the energy source is output from the energy-source output unit.

8. The ablation-treatment-tool control device according to claim 6, wherein the area calculation unit is configured to:
    receive an endoscopic image of the ileal mucosa from an endoscope;
    calculate an area of a new treatment region every time the ablation treatment is performed on the ileal mucosa, on the basis of the endoscopic image; and
    calculate the total treatment area by adding up the calculated areas of the treatment regions.

9. An ablation system comprising:
    an ablation treatment tool; and
    the ablation-treatment-tool control device according to claim 2, which is configured to control the ablation treatment tool.

10. The ablation system according to claim 9, further comprising an endoscope that has a treatment-tool channel and is configured to be inserted into the ileum, wherein the ablation treatment tool is configured to be inserted through the treatment-tool channel.

* * * * *